(12) United States Patent
Mazanec

(10) Patent No.: US 11,564,046 B2
(45) Date of Patent: Jan. 24, 2023

(54) PROGRAMMING OF COCHLEAR IMPLANT ACCESSORIES

(71) Applicant: Envoy Medical Corporation, White Bear Lake, MN (US)

(72) Inventor: Paul R. Mazanec, Ham Lake, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 323 days.

(21) Appl. No.: 17/006,467

(22) Filed: Aug. 28, 2020

(65) Prior Publication Data

US 2022/0070594 A1 Mar. 3, 2022

(51) Int. Cl.
*H04R 25/00* (2006.01)
*A61N 1/36* (2006.01)
*A61N 1/05* (2006.01)

(52) U.S. Cl.
CPC ......... *H04R 25/554* (2013.01); *A61N 1/0541* (2013.01); *A61N 1/36038* (2017.08); *H04R 25/556* (2013.01); *H04R 25/558* (2013.01)

(58) Field of Classification Search
CPC .. H04R 25/554; H04R 25/556; H04R 25/558; A61N 1/0541; A61N 1/36038; A61N 1/37235
See application file for complete search history.

(56) References Cited

U.S. PATENT DOCUMENTS

| 2,827,041 | A | 3/1958 | Pierson |
| 4,400,590 | A | 8/1983 | Michelson |
| 4,495,384 | A | 1/1985 | Scott et al. |
| 4,729,366 | A | 3/1988 | Schaefer |
| 4,850,962 | A | 7/1989 | Schaefer |

(Continued)

FOREIGN PATENT DOCUMENTS

| CN | 104394930 A | 3/2015 |
| CN | 110086237 A | 8/2019 |

(Continued)

OTHER PUBLICATIONS

PCT International Search Report and Written Opinion dated Jan. 5, 2022 for related Intl. App. No. PCT/US2021/047855, 12 pages.

*Primary Examiner* — Brian Ensey
(74) *Attorney, Agent, or Firm* — Fredrikson & Byron, P.A.

(57) ABSTRACT

Pairing systems for pairing external devices to a cochlear implant system can comprise an external housing and an external pairing system. The external housing may comprise a first surface and one or more compartments, each configured to house an external device capable of wirelessly interfacing with an implantable cochlear implant system. The external pairing device may comprise a second surface and one or more corresponding near field communication devices. The near field communication devices may be arranged such that the first surface of the external housing can be aligned with the second surface of the external pairing device in such a way that each of the near field communication devices aligns with a corresponding compartment of the external housing. The external pairing device can provide communication between a programming device and external devices contained within compartments of the external housing via one or more corresponding near field communication devices.

22 Claims, 15 Drawing Sheets

(56) References Cited

U.S. PATENT DOCUMENTS

| | | | |
|---|---|---|---|
| 4,918,745 A | 4/1990 | Hutchison | |
| 5,540,095 A | 7/1996 | Sherman et al. | |
| 5,762,583 A | 6/1998 | Adams et al. | |
| 6,195,585 B1 | 2/2001 | Karunasiri et al. | |
| 6,212,431 B1 | 4/2001 | Hahn et al. | |
| 6,259,951 B1 | 7/2001 | Kuzma et al. | |
| 6,272,382 B1 | 8/2001 | Faltys et al. | |
| 6,308,101 B1 | 10/2001 | Faltys et al. | |
| 6,358,281 B1 | 3/2002 | Berrang et al. | |
| 6,554,329 B1 | 4/2003 | DeBlock et al. | |
| 7,225,028 B2 | 5/2007 | Della Santina et al. | |
| 7,319,906 B2 | 1/2008 | Kuzma et al. | |
| 7,524,278 B2 | 4/2009 | Madsen et al. | |
| 8,655,449 B2 | 2/2014 | Haller et al. | |
| 9,504,076 B2 * | 11/2016 | El-Hoiydi | H04W 4/21 |
| 9,539,430 B2 | 1/2017 | Mishra et al. | |
| 9,716,952 B2 | 7/2017 | Mauger | |
| 2002/0039425 A1 | 4/2002 | Burnett et al. | |
| 2002/0099421 A1 | 7/2002 | Goldsmith et al. | |
| 2005/0033384 A1 | 2/2005 | Sacha | |
| 2005/0197677 A1 | 9/2005 | Stevenson | |
| 2006/0122664 A1 | 6/2006 | Sacha et al. | |
| 2006/0183965 A1 | 8/2006 | Kasic, II et al. | |
| 2008/0195179 A1 | 8/2008 | Quick | |
| 2008/0300658 A1 | 12/2008 | Meskens | |
| 2009/0018616 A1 | 1/2009 | Quick et al. | |
| 2009/0082831 A1 | 3/2009 | Paul et al. | |
| 2009/0187233 A1 | 7/2009 | Stracener | |
| 2009/0192565 A1 | 7/2009 | Lee et al. | |
| 2010/0030012 A1 | 2/2010 | Meskens | |
| 2010/0042183 A1 | 2/2010 | Beck | |
| 2010/0317913 A1 | 12/2010 | Conn et al. | |
| 2011/0082521 A1 | 4/2011 | Botros et al. | |
| 2011/0116669 A1 | 5/2011 | Karunasir | |
| 2011/0137180 A1 | 6/2011 | Johnson et al. | |
| 2011/0144719 A1 | 6/2011 | Perkins et al. | |
| 2011/0160808 A1 | 6/2011 | Lyden et al. | |
| 2011/0280426 A1 | 11/2011 | Bachler | |
| 2011/0295331 A1 | 12/2011 | Wells et al. | |
| 2012/0215285 A1 | 8/2012 | Tahmasian et al. | |
| 2012/0277835 A1 | 11/2012 | Della Santina et al. | |
| 2013/0018216 A1 | 1/2013 | Beckerle et al. | |
| 2013/0023953 A1 | 1/2013 | van den Honert | |
| 2013/0193914 A1 | 8/2013 | Gaddam et al. | |
| 2013/0223664 A1 | 8/2013 | Meskens et al. | |
| 2013/0238055 A1 | 9/2013 | Marnfeldt et al. | |
| 2013/0268025 A1 | 10/2013 | Ranu | |
| 2013/0278226 A1 | 10/2013 | Cong et al. | |
| 2013/0317584 A1 | 11/2013 | Stevenson et al. | |
| 2014/0058482 A1 | 2/2014 | Gupta et al. | |
| 2014/0247954 A1 | 9/2014 | Hall et al. | |
| 2014/0270211 A1 | 9/2014 | Solum et al. | |
| 2014/0275730 A1 | 9/2014 | Lievens et al. | |
| 2014/0309712 A1 | 10/2014 | Masaki et al. | |
| 2014/0350652 A1 | 11/2014 | Suwito | |
| 2015/0125012 A1 | 5/2015 | Sabin | |
| 2015/0174416 A1 | 6/2015 | Angara et al. | |
| 2015/0224312 A1 | 8/2015 | Platz et al. | |
| 2015/0256945 A1 | 9/2015 | Mazanec | |
| 2015/0374988 A1 | 12/2015 | Laudanski | |
| 2015/0375003 A1 | 12/2015 | Meskens | |
| 2016/0227333 A1 | 8/2016 | Babico | |
| 2017/0043162 A1 | 2/2017 | Lopez-Poveda | |
| 2017/0077938 A1 | 3/2017 | Heubi | |
| 2017/0094396 A1 * | 3/2017 | Chandramohan | H04R 1/345 |
| 2017/0161449 A1 | 6/2017 | Meskens | |
| 2017/0259072 A1 | 9/2017 | Newham et al. | |
| 2017/0360364 A1 | 12/2017 | Heasman et al. | |
| 2018/0028811 A1 | 2/2018 | Van Gerwen et al. | |
| 2018/0028827 A1 | 2/2018 | Schilling et al. | |
| 2018/0041848 A1 | 2/2018 | Nielsen et al. | |
| 2018/0050197 A1 | 2/2018 | Mazanec et al. | |
| 2018/0050198 A1 | 2/2018 | Mazanec et al. | |
| 2018/0050203 A1 | 2/2018 | Mazanec et al. | |
| 2018/0059870 A1 | 3/2018 | Krah | |
| 2018/0264269 A1 | 9/2018 | Meadows | |
| 2018/0317027 A1 | 11/2018 | Bolner et al. | |
| 2018/0333577 A1 | 11/2018 | Nygard et al. | |
| 2018/0361151 A1 | 12/2018 | Ridler et al. | |
| 2019/0045308 A1 | 2/2019 | Chen et al. | |
| 2019/0046116 A1 | 2/2019 | Shah et al. | |
| 2020/0054877 A1 | 2/2020 | Calixto et al. | |
| 2020/0238075 A1 | 7/2020 | Mazanec et al. | |
| 2020/0269034 A1 | 8/2020 | Mazanec et al. | |
| 2020/0269035 A1 | 8/2020 | Mazanec et al. | |
| 2020/0269047 A1 | 8/2020 | Mazanec et al. | |
| 2020/0269048 A1 | 8/2020 | Mazanec et al. | |
| 2020/0269057 A1 | 8/2020 | Mazanec et al. | |
| 2020/0269058 A1 | 8/2020 | Mazanec et al. | |
| 2021/0084417 A1 * | 3/2021 | Bagazov | H04B 5/0006 |
| 2021/0135704 A1 | 5/2021 | El-Hoiydi et al. | |
| 2021/0187293 A1 | 6/2021 | Friedling | |
| 2021/0361194 A1 | 11/2021 | Arab et al. | |

FOREIGN PATENT DOCUMENTS

| | | |
|---|---|---|
| DE | 4419070 A1 | 12/1994 |
| DE | 60107062 T2 | 11/2005 |
| DE | 102013214049 B4 | 3/2015 |
| EP | 1043914 A2 | 10/2000 |
| EP | 1683544 B1 | 11/2010 |
| EP | 2884766 B1 | 2/2018 |
| EP | 3120579 B1 | 2/2020 |
| TW | 201142830 A | 12/2011 |
| WO | 2007137032 A2 | 11/2007 |
| WO | 2010056768 A1 | 5/2010 |
| WO | 2014037888 A1 | 3/2014 |
| WO | 2015077773 A1 | 5/2015 |
| WO | 2016122606 A1 | 8/2016 |
| WO | 2017100866 A1 | 6/2017 |
| WO | 2018035329 A1 | 2/2018 |
| WO | 2018144732 A1 | 8/2018 |
| WO | 2020172500 A1 | 8/2020 |

\* cited by examiner

|  | Programmer | Charger | Smartphone/Tablet | Smartwatch/Wearable | Fob | External Audio Source | Remote Audio Pickup |
|---|---|---|---|---|---|---|---|
| On/Off | X | X | X | X | X | | |
| Switch Profile/ Transfer Function | X | X | X | X | X | | |
| Adjust Volume | X | X | X | X | X | | |
| Adjust Mix | X | X | X | X | | | |
| Receive Audio Stream | X | | X | X | | | |
| Broadcast Audio Stream | X | | X | X | | X | X |
| Emergency Shut-off | X | X | X | X | X | | |

FIG. 14

PROGRAMMING OF COCHLEAR IMPLANT ACCESSORIES

BACKGROUND

Cochlear implant systems are systems which may be at least partially implanted surgically into and around the cochlea, the hearing organ of the ear, to provide improved hearing to a patient. Cochlear implant systems may also be in communication with various devices internal to the wearer as well as one or more external devices.

External devices may comprise a variety of components that can be used to interact with the cochlear implant system or in tandem with the cochlear implant system to provide a better hearing experience for the patient. However in some cases, external devices may need to be paired with the cochlear implant system prior to them communicating with the cochlear implant system. Manually pairing the various external devices with a wearer's implant system may prove to be costly both monetarily as well as in time. For example, an audiologist may need to electrically charge and manually pair various devices with a wearer's cochlear implant system one-by-one. Charging each device enough to turn on and pair each device to the wearer's cochlear implant system can take an undesirably long time, and additional device to be paired can compound the delay. Furthermore, manually pairing each external device leaves room for human error, such as forgetting to charge one or more external devices or forgetting to pair one or more external devices before sending such a device home with the wearer. This may subsequently require a second appointment to fix any errors or pair missed devices.

SUMMARY

Some aspects of the disclosure are generally directed toward a pairing system for pairing one or more external devices to a cochlear implant system. In some examples, the pairing system may comprise an external housing, such as a box, a briefcase, or the like. The external housing may have a first surface as well as a plurality of compartments arranged in a first configuration such that each of the plurality of compartments has a unique position within the external housing relative to the first surface. Each of the plurality of compartments may be additionally configured to house an external device capable of wirelessly interfacing with a cochlear implant system, such as a fully implantable cochlear implant system. In some embodiments, each of the plurality of compartments may be shaped as to receive a unique corresponding external device however alternative shapes may be used.

Additionally or alternatively, the pairing device may include an external pairing device, such as a mat, a tabletop, or the like. The external pairing device may comprise a second surface as well as a plurality of near field communication devices. In some embodiments, the plurality of near field communication devices may be arranged in a configuration corresponding to the first configuration and/or arranged in the first configuration relative to the second surface such that the first surface of the external housing can be aligned with the second surface of the external pairing device in such a way that each of the plurality of near field communication devices aligns with a corresponding one of the plurality of compartments of the external housing. In some embodiments, the plurality of near field communication devices may be located beneath the second surface. The external pairing device may be configured to provide communication between a programming device and one or more external devices, each contained with a different compartment of the external housing, via one or more corresponding near field communication devices of the external pairing device.

In some embodiments, the external pairing device may be configured to electrically charge one or more external devices, each contained in a corresponding compartment of the external housing, via a corresponding one or more near field communication device of the external pairing device when the external housing is positioned proximate the external pairing device and each of the plurality of near field communication devices aligns with a corresponding one of the plurality of compartments of the external housing. Additionally or alternatively, each near field communication device comprises a coil configured to facilitate communication with and charging of an external device within a corresponding compartment and having a corresponding coil.

In some embodiments, systems may comprise a cochlear implant system, a programming device, and one or more external devices. The cochlear implant system may comprise a cochlear electrode, a stimulator, a signal processor, and an implantable battery and/or communication module. In some embodiments, the programming device is configured to communicate with each of the one or more external devices via corresponding near field communication devices of the external pairing device and provide information to each of the one or more external devices to enable communication between each external device and the cochlear implant system.

Additionally or alternatively, the programming device may be configured to provide information to each of the one or more external devices to enable communication between each external device and the implantable battery and/or communication module of the cochlear implant system.

BRIEF DESCRIPTION OF THE DRAWINGS

FIG. 14 is a chart showing the various parameters that are adjustable by each of a variety of external devices.

DETAILED DESCRIPTION

Figure 1:
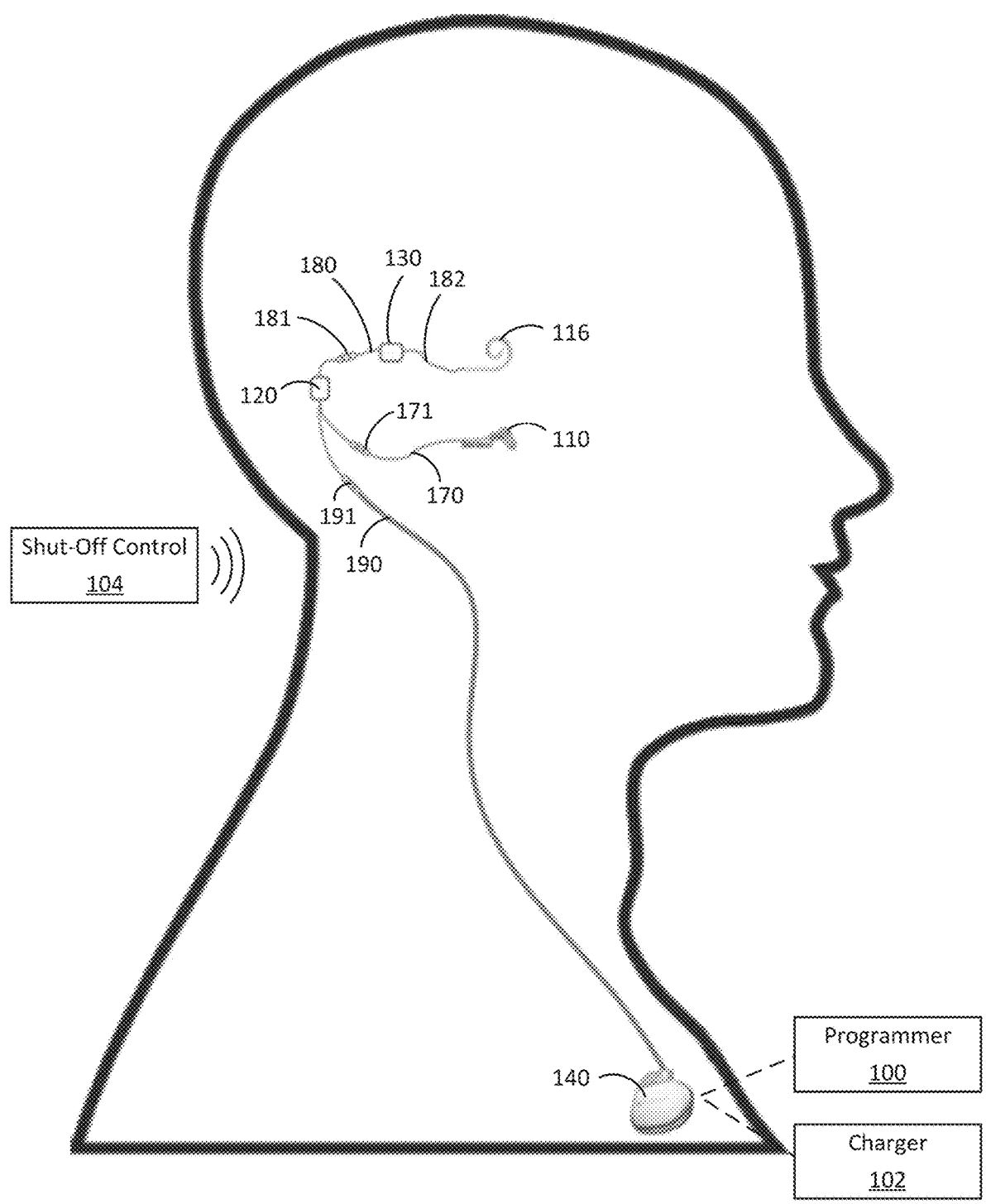
FIG. 1 shows a schematic illustration of a fully implantable cochlear implant system.

FIG. 1 shows a schematic illustration of a fully implantable cochlear implant system. The system of FIG. 1 includes a middle ear sensor 110 in communication with a signal processor 120. The middle ear sensor 110 can be configured to detect incoming sound waves, for example, using the ear structure of a patient. The signal processor 120 can be configured to receive a signal from the middle ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 120 can be based on a lookup table or other programmed (e.g., in memory) correspondence between the input signal from the middle ear sensor 110 and the output signal. While not necessarily based explicitly on a function, the relationship between the input to the signal processor 120 (e.g., from the middle ear sensor 110) and the output of the signal processor 120 is referred to as the transfer function of the signal processor 120.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the middle ear sensor 110 detects audio signals, for example, using features of the patient's ear anatomy as described elsewhere herein and in U.S. Patent Publication No. 2013/0018216, which is hereby incorporated by reference in its entirety. The signal processor 120 can receive such signals from the middle ear sensor 110 and produce an output to the electrical stimulator 130 based on the transfer function of the signal processor 120. The electrical stimulator 130 can then stimulate one or more contact electrodes of the cochlear electrode 116 based on the received signals from the signal processor 120.

Figure 2:
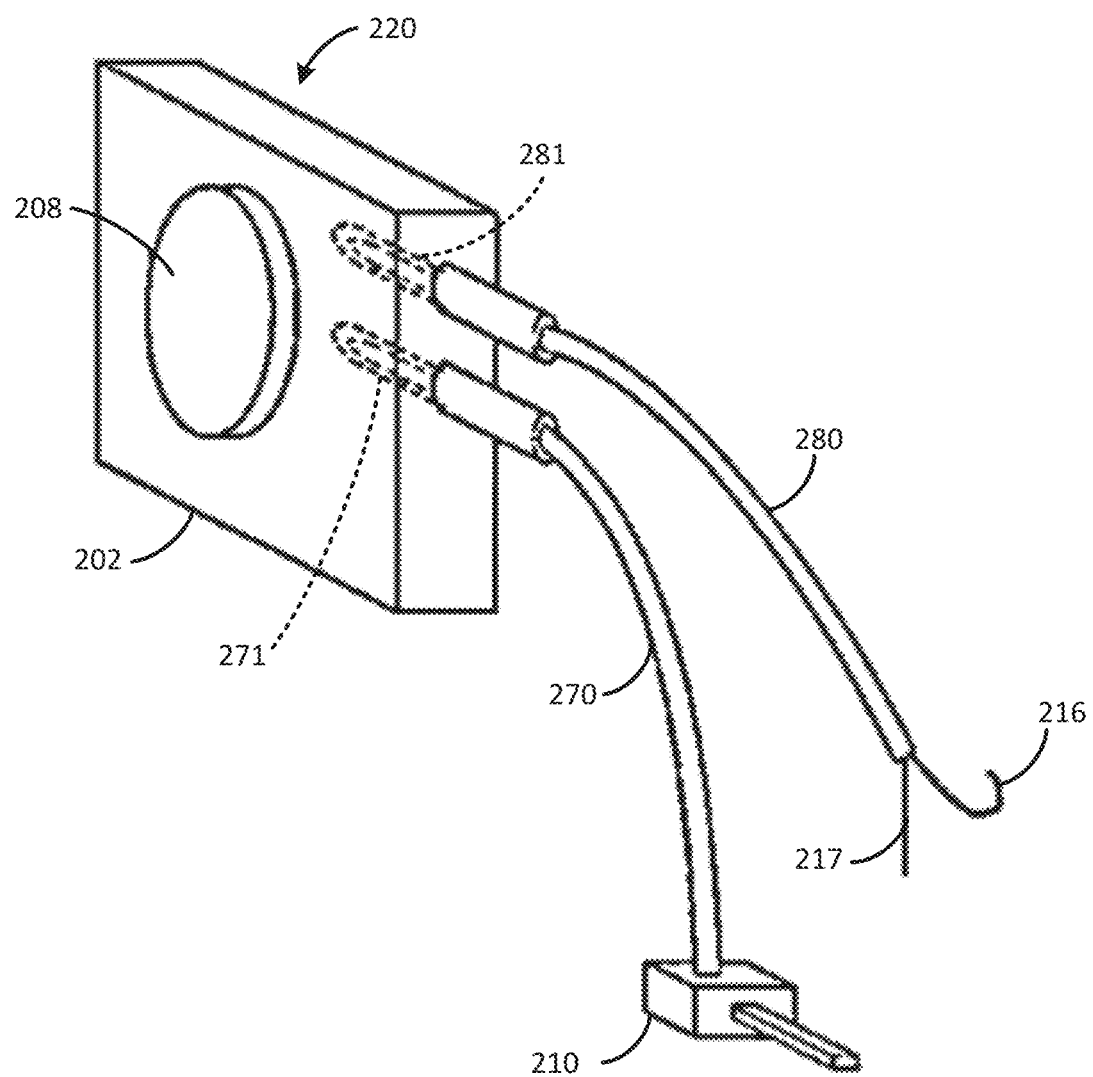
FIG. 2 shows an embodiment of a fully implantable cochlear implant.

Referring to FIG. 2, an embodiment of a fully implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in U.S. Patent Publication No. 2013/0018216, which is incorporated by reference. In other examples, processor 220 is configured to receive power and/or data from other sources, such as an implantable battery and/or communication module as shown in FIG. 1. Such battery and/or communication module can be implanted, for example, into the pectoral region of the patient in order to provide adequate room for larger equipment (e.g., a relatively large battery) for prolonged operation (e.g., longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3:
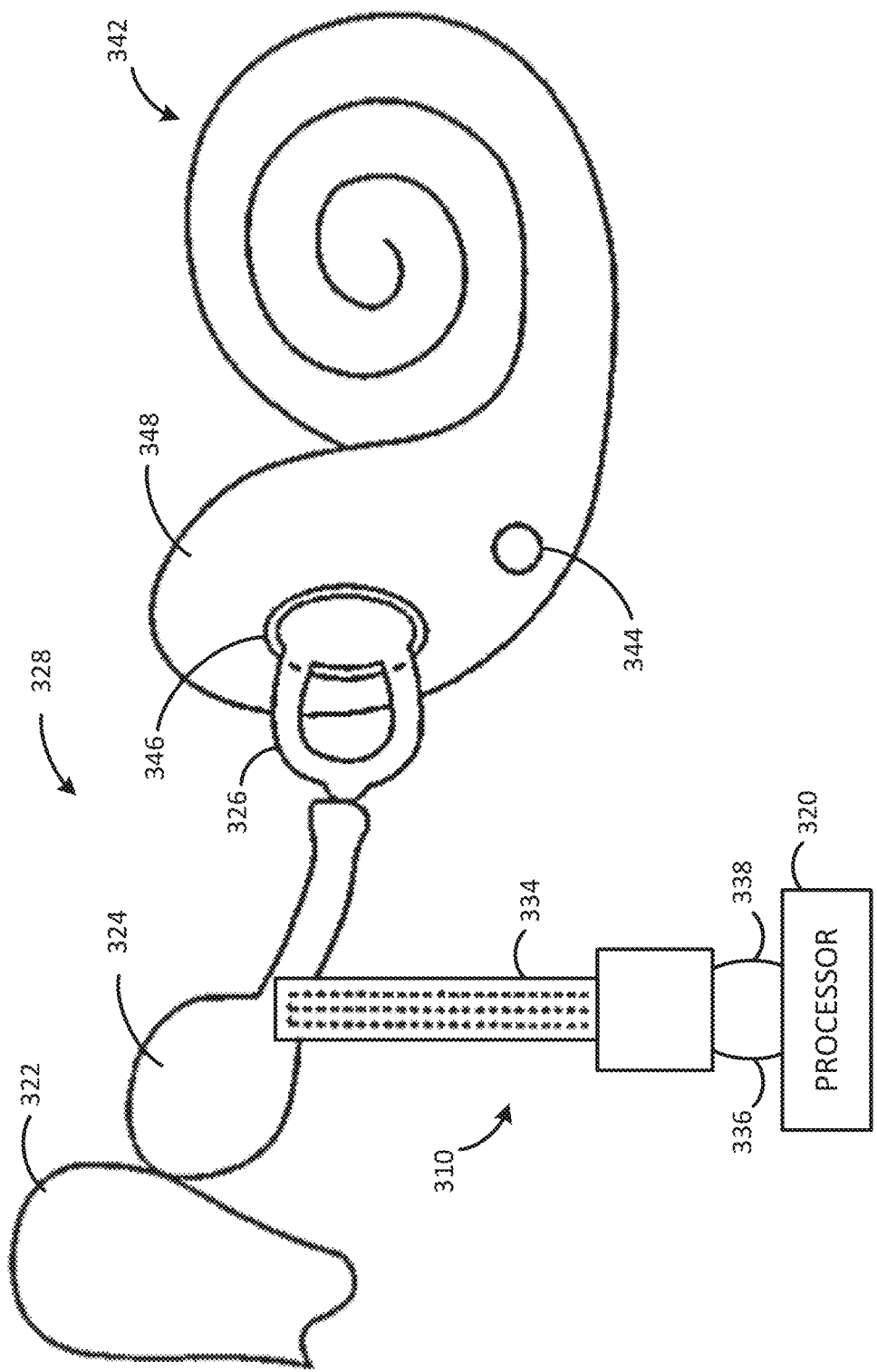
FIG. 3 illustrates an embodiment of an exemplary middle ear sensor for use in conjunction with anatomical features of a patient

FIG. 3 illustrates embodiments of an exemplary middle ear sensor for use in conjunction with anatomical features of a patient. Referring to FIG. 3, an embodiment of the sensor 310 of a fully implantable cochlear implant is shown. Also shown are portions of the subject's anatomy, which includes, if the subject is anatomically normal, at least the malleus 322, incus 324, and stapes 326 of the middle ear 328, and the cochlea 348, oval window 346, and round window 344 of the inner ear 342. Here, the sensor 310 is touching the incus 324. Further, although not shown in a drawing, the sensor 310 may be in operative contact with the tympanic membrane or the stapes, or any combination of the tympanic membrane, malleus 322, incus 324, or stapes 326.

FIG. 3 illustrates an exemplary middle ear sensor for use with systems described herein. However, other middle ear sensors can be used, such as sensors using microphones or other sensors capable of receiving an input corresponding to detected sound and outputting a corresponding signal to the signal processor. Additionally or alternatively, systems can include other sensors configured to output a signal representative of sound received at or near a user's ear, such as a microphone or other acoustic pickup located in the user's outer ear or implanted under the user's skin. Such devices may function as an input source, for example, to the signal processor such that the signal processor receives an input signal from the input source and generates and output one or more stimulation signals according to the received input signal and the signal processor transfer function.

Referring back to FIG. 1, the signal processor 120 is shown as being in communication with the middle ear sensor 110, the electrical stimulator 130, and the implantable battery and/or communication module 140. As described elsewhere herein, the signal processor 120 can receive input signals from the middle ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140.

In some embodiments, the implantable battery and/or communication module 140 can communicate with external devices, such as a programmer 100 and/or a battery charger 102. The battery charger 102 can wirelessly charge the battery in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and charger 102 can be separate devices or can be integrated into a single device.

In the illustrated example of FIG. 1, the signal processor 120 is connected to the middle ear sensor 110 via lead 170. In some embodiments, lead 170 can provide communication between the signal processor 120 and the middle ear sensor 110. In some embodiments, lead 170 can include a plurality of isolated conductors providing a plurality of communication channels between the middle ear sensor 110 and the signal processor 120. The lead 170 can include a coating such as an electrically insulating sheath to minimize any conduction of electrical signals to the body of the patient. In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and middle ear sensor 110. For example, with reference to FIG. 1, in some embodiments, lead 170 can include a first lead extending from the middle ear sensor 110 having one of a male (e.g., 672) or a female (e.g., 673) connector and a second lead extending from the signal processor 120 having the other of the male or female connector. The first and second leads can be connected at detachable connector 171 in order to facilitate communication between the middle ear sensor 110 and the signal processor 120.

In other examples, a part of the detachable connector 171 can be integrated into one of the middle ear sensor 110 and the signal processor 120. For example, in an exemplary embodiment, the signal processor 120 can include a female connector integrated into a housing of the signal processor 120. Lead 170 can extend fully from the middle ear sensor 110 and terminate at a corresponding male connector for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the middle ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, middle ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a module configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. In an exemplary procedure, an implanted signal processor 120 can be disconnected from the electrical stimulator 130 by disconnecting detachable connector 181, from the middle ear sensor 110 by disconnecting detachable connector 171, and from the implantable battery and/or communication module 140 by disconnecting detachable connector 191. Thus, the signal processor 120 can be removed from the patient while other components such as the electrical stimulator 130, cochlear electrode 116, middle ear sensor 110, and battery and/or communication module can remain in place in the patient.

After the old signal processor is removed, a new signal processor can be connected to the electrical stimulator 130, middle ear sensor 110, and implantable battery and/or communication module 140 via detachable connectors 181, 171, and 191, respectively. Thus, the signal processor (e.g., 120) can be replaced, repaired, upgraded, or any combination thereof, without affecting the other system components. This can reduce, among other things, the risk, complexity, duration, and recovery time of such a procedure. In particular, the cochlear electrode 116 can be left in place in the patient's cochlea while other system components can be adjusted, reducing trauma to the patient's cochlear tissue.

Such modularity of system components can be particularly advantageous when replacing a signal processor 120, such as described above. Processor technology continues to improve and will likely continue to markedly improve in the future, making the signal processor 120 a likely candidate for significant upgrades and/or replacement during the patient's lifetime. Additionally, in embodiments such as the embodiment shown in FIG. 1, the signal processor 120 communicates with many system components. For example, as shown, the signal processor 120 is in communication with each of the electrical stimulator 130, the middle ear sensor 110, and the implantable battery and/or communication module 140. Detachably connecting such components with the signal processor 120 (e.g., via detachable connectors 181, 171, and 191) enables replacement of the signal processor 120 without disturbing any other components. Thus, in the event of an available signal processor 120 upgrade and/or a failure of the signal processor 120, the signal processor 120 can be disconnected from other system components and removed.

While many advantages exist for a replaceable signal processor 120, the modularity of other system components can be similarly advantageous, for example, for upgrading any system component. Similarly, if a system component (e.g., the middle ear sensor 110) should fail, the component can be disconnected from the rest of the system (e.g., via detachable connector 171) and replaced without disturbing the remaining system components. In another example, even a rechargeable battery included in the implantable battery and/or communication module 140 may eventually wear out and need replacement. The implantable battery and/or communication module 140 can be replaced or accessed (e.g., for replacing the battery) without disturbing other system components. Further, as discussed elsewhere herein, when the implantable battery and/or communication module 140 is implanted in the pectoral region of the patient, such as in the illustrated example, such a procedure can leave the patient's head untouched, eliminating unnecessarily frequent access beneath the skin.

While various components are described herein as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/ stimulator/cochlear electrode component does not get removed from a patient due to potential damage to the cochlear tissue into which the cochlear electrode is implanted, system upgrades are still possible. For example, in some embodiments, a module signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 4:
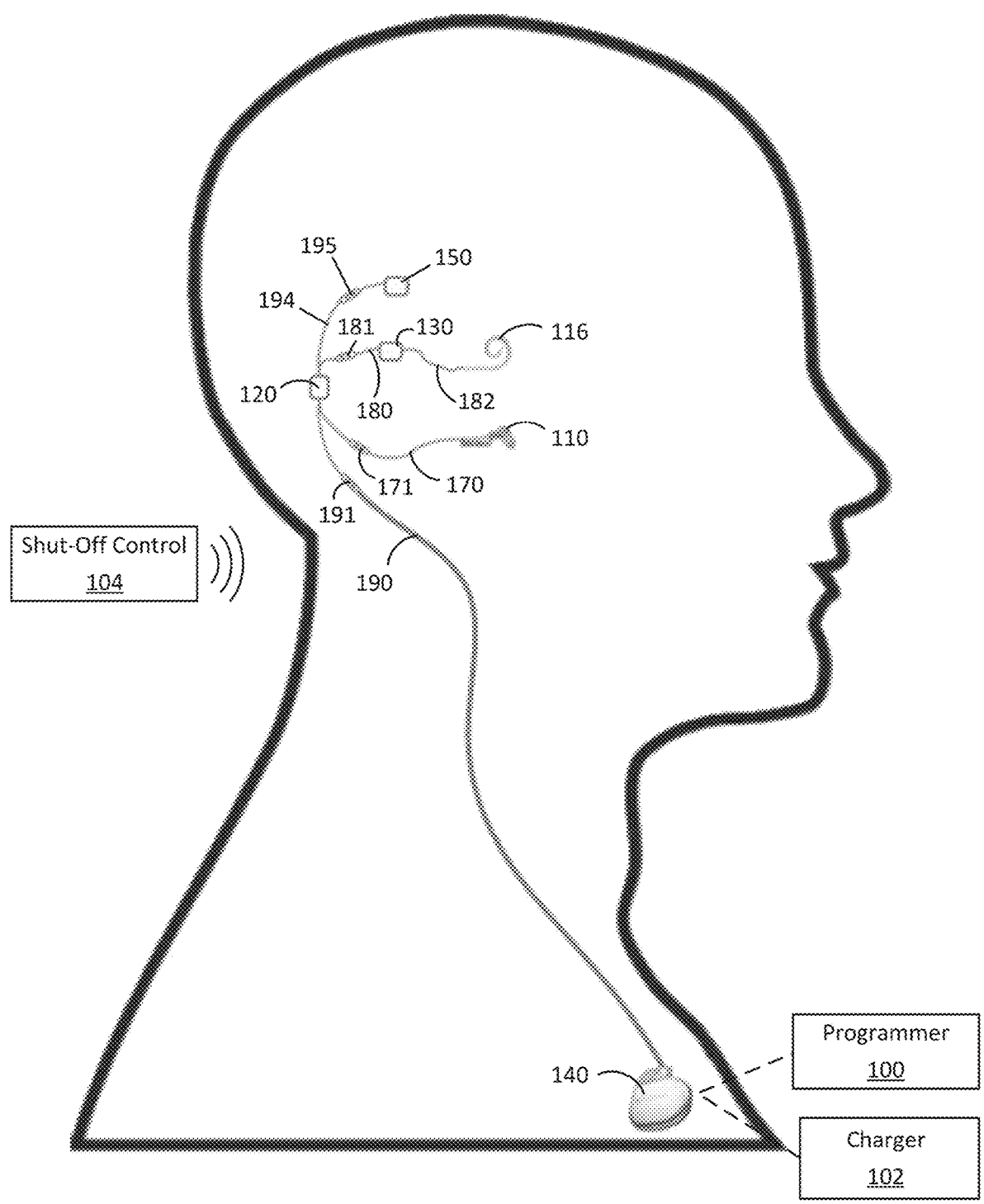
FIG. 4 is a schematic diagram illustrating an exemplary implantable system including an acoustic stimulator.

FIG. 4 is a schematic diagram illustrating an exemplary implantable system including an acoustic stimulator. The acoustic stimulator can be implanted proximate the patient's ossicular chain and can be in communication with a signal processor via lead 194 and detachable connector 195. The signal processor can behave as described elsewhere herein and can be configured to cause acoustic stimulation of the ossicular chain via the acoustic stimulator in in response to input signals from the middle ear sensor according to a transfer function of the signal processor.

The acoustic stimulator of FIG. 4 can be used similarly to the electrical stimulator as described elsewhere herein. For instance, an acoustic stimulator can be mechanically coupled to a patient's ossicular chain upon implanting the system and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

With further reference to FIGS. 1 and 4, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external devices, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the middle ear sensor).

With reference back to FIG. 1, as described elsewhere herein, the implantable battery and/or communication module can be used to provide power and/or data (e.g., processing instructions) to other system components via lead 190. Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component). Various systems and methods can be employed to improve the communication ability between system components.

Figure 5A:
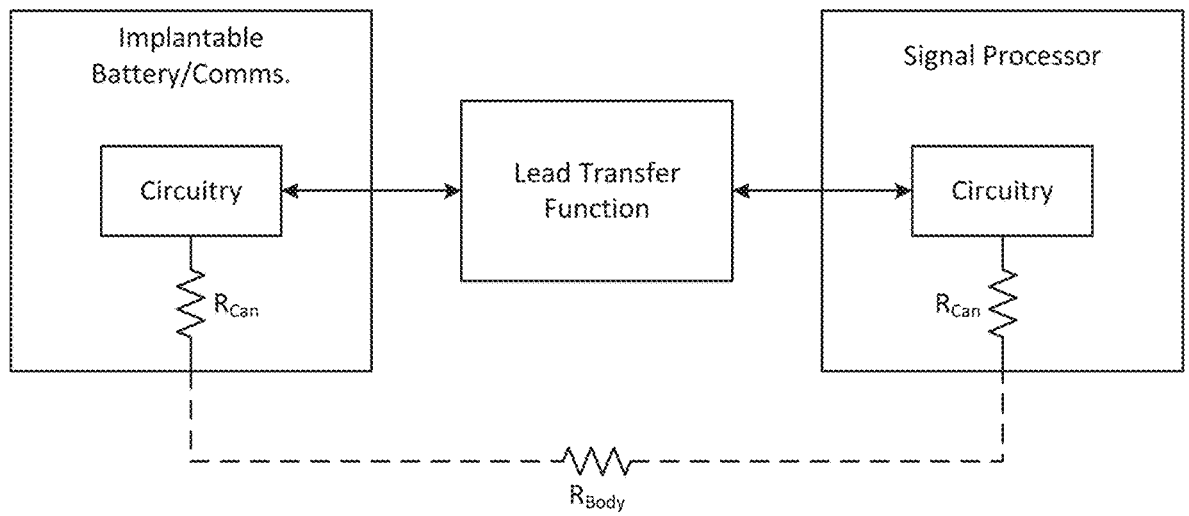
FIG. 5A is a high level electrical schematic showing communication between the implantable battery and/or communication module and the signal processor.

FIG. 5A is a high level electrical schematic showing communication between the implantable battery and/or communication module and the signal processor. In the illustrated embodiment, the implantable battery and/or communication module includes circuitry in communication with circuitry in the signal processor. Communication between the circuitry in the implantable battery and/or communication module and the signal processor can be facilitated by a lead (190), represented by the lead transfer function. The lead transfer function can include, for example, parasitic resistances and capacitances between the leads connecting the implantable battery and/or communication module and the signal processor and the patient's body and/or between two or more conductors that make up the lead (e.g., 191). Signals communicated from the circuitry of the implantable battery and/or communication module to the circuitry in the signal processor can include electrical power provided to operate and/or stimulate system components (e.g., the middle ear sensor, signal processor, electrical and/or acoustic stimulator, and/or cochlear electrode) and/or data (e.g., processing data regarding the transfer function of the signal processor).

As discussed elsewhere herein, the body of the patient provides an electrical path between system components, such as the "can" of the implantable battery and/or communication module and the "can" of the signal processor. This path is represented in FIG. 5A by the flow path through $R_{Body}$. Thus, the patient's body can provide undesirable signal paths which can negatively impact communication between components. To address this, in some embodiments, operating circuitry in each component can be substantially isolated from the component "can" and thus the patient's body. For example, as shown, resistance $R_{Can}$ is positioned between the circuitry and the "can" of both the implantable battery and/or communication module and the signal processor.

While being shown as $R_{Can}$ in each of the implantable battery and/or communication module and the signal processor, it will be appreciated that the actual value of the resistance between the circuitry and respective "can" of different elements is not necessarily equal. Additionally, $R_{Can}$ need not include purely a resistance, but can include other components, such as one or more capacitors, inductors, and the like. That is, $R_{Can}$ can represent an insulating circuit including any variety of components that act to increase the impedance between circuitry within a component and the "can" of the component. Thus, $R_{Can}$ can represent an impedance between the operating circuitry of a component and the respective "can" and the patient's tissue. Isolating the circuitry from the "can" and the patient's body acts to similarly isolate the circuitry from the "can" of other components, allowing each component to operate with reference to a substantially isolated component ground. This can eliminate undesired communication and interference between system components and/or between system components and the patient's body.

Figure 5B:
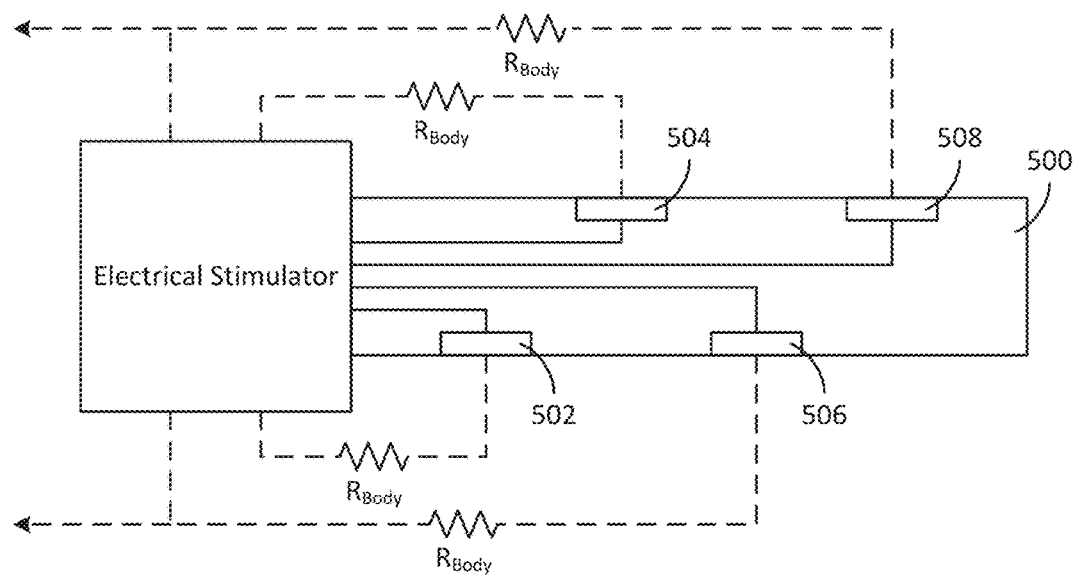
FIG. 5B illustrates an exemplary schematic diagram illustrating a cochlear electrode having a plurality of contact electrodes and fixedly or detachably connected to an electrical stimulator.

For example, as described elsewhere herein, in some examples, an electrical stimulator can provide an electrical stimulus to one or more contact electrodes on a cochlear electrode implanted in a patient's cochlear tissue. FIG. 5B illustrates an exemplary schematic diagram illustrating a cochlear electrode having a plurality of contact electrodes and fixedly or detachably connected to an electrical stimulator. As shown, the cochlear electrode 500 has four contact electrodes 502, 504, 506, and 508, though it will be appreciated that any number of contact electrodes is possible. As described elsewhere herein, the electrical stimulator can provide electrical signals to one or more such contact electrodes in response to an output from the signal processor according to the transfer function thereof and a received input signal.

Because each contact electrode 502-508 is in contact with the patient's cochlear tissue, each is separated from the "can" of the electrical stimulator (as well as the "cans" of other system components) via the impedance of the patient's tissue, shown as $R_{Body}$. Thus, if the circuitry within various system components did not have sufficiently high impedance (e.g., $R_{Can}$) to the component "can", electrical signals may stimulate undesired regions of the patient's cochlear tissue. For instance, stimulation intended for a particular contact electrode (e.g., 502) may lead to undesired stimulation of other contact electrodes (e.g., 504, 506, 508), reducing the overall efficacy of the system. Minimizing the conductive paths between system components (e.g., to the contact electrodes of a cochlear electrode) due to the patient's body, such as by incorporating impedances between component circuitry and the corresponding "can" via $R_{Can}$, can therefore improve the ability to apply an electrical stimulus to only a desired portion of the patient's body.

It will be appreciated that the term $R_{Body}$ is used herein to generally represent the resistance and/or impedance of the patient's tissue between various components and does not refer to a specific value. Moreover, each depiction or $R_{Body}$ in the figures does not necessarily represent the same value of resistance and/or impedance as the others.

Figure 6A:
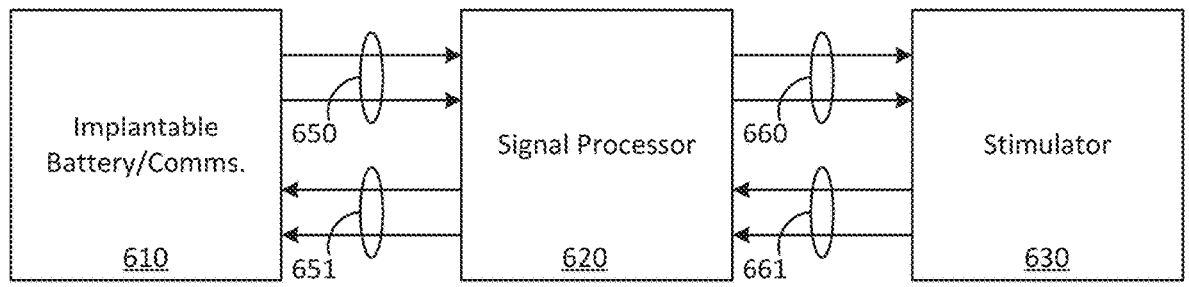
FIG. 6A shows a high level schematic diagram illustrating an exemplary communication configuration between an implantable battery and/or communication module, a signal processor, and a stimulator in an exemplary cochlear implant system.

FIG. 6A shows a high level schematic diagram illustrating an exemplary communication configuration between an implantable battery and/or communication module, a signal processor, and a stimulator. In the example of FIG. 6A, the implantable battery and/or communication module 610 is in two-way communication with the signal processor 620. For instance, the implantable battery and/or communication module 610 can communicate power and/or data signals 650 to the signal processor 620. In some examples, the power and data signals 650 can be included in a single signal generated in the implantable battery and/or communication module 610 and transmitted to the signal processor 620. Such signals can include, for example, a digital signal transmitted with a particular clock rate, which in some embodiments, can be adjustable, for example, via the implantable battery and/or communication module 610.

In some embodiments, the signal processor 620 can communicate information to the implantable battery and/or communication module 610 (e.g., 651), for example, feedback information and/or requests for more power, etc. The implantable battery and/or communication module 610 can, in response, adjust its output to the signal processor 620 (e.g., an amplitude, duty cycle, clock rate, etc.) in order to accommodate for the received feedback (e.g., to provide more power, etc.). Thus, in some such examples, the implantable battery and/or communication module 610 can communicate power and data (e.g., 650) to the signal processor 620, and the signal processor 620 can communicate various data back to the implantable battery and/or communication module 610 (e.g., 651).

In some embodiments, similar communication can be implemented between the signal processor 620 and the stimulator 630, wherein the signal processor 620 provides power and data to the stimulator 630 (e.g., 660) and receives data in return from the stimulator 630 (e.g., 661). For example, the signal processor 620 can be configured to output signals (e.g., power and/or data) to the stimulator 630 (e.g., based on received inputs from a middle ear sensor or other device) via a similar communication protocol as implemented between the implantable battery and/or communication module 610 and the signal processor 620. Similarly, in some embodiments, the stimulator can be configured to provide feedback signals to the signal processor, for example, representative of an executed stimulation process. Additionally or alternatively, the stimulator may provide diagnostic information, such as electrode impedance and neural response telemetry or other biomarker signals.

Figure 6B:
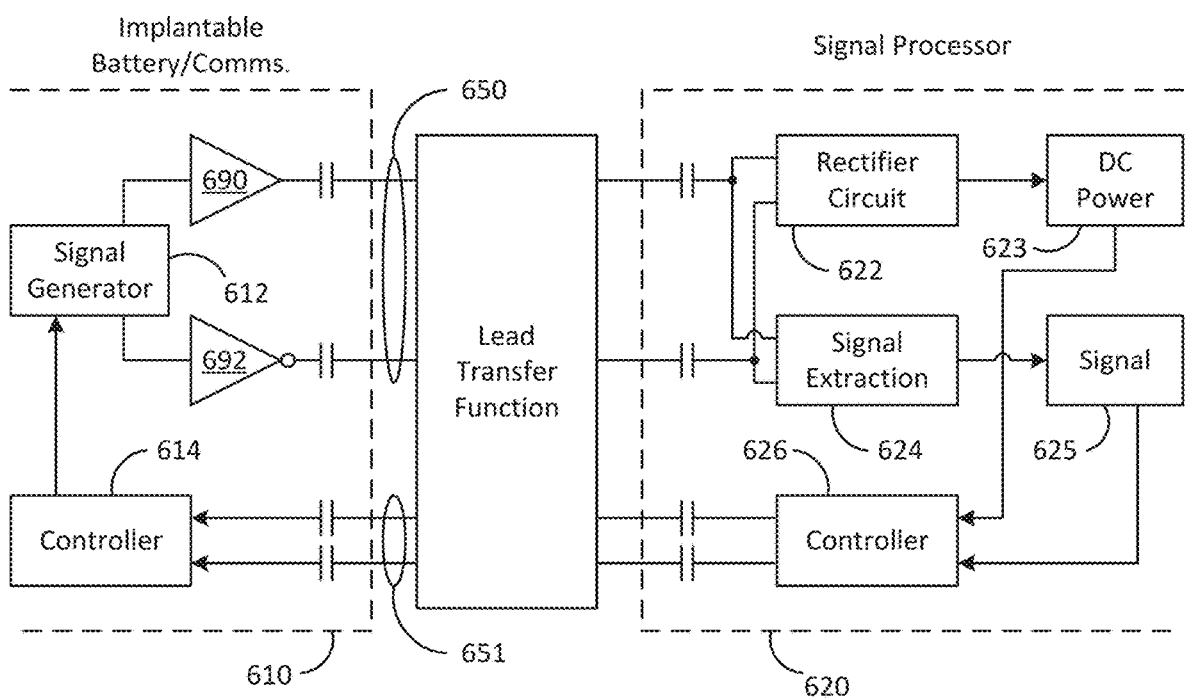
FIG. 6B is a schematic diagram illustrating exemplary electrical communication between an implantable battery and/or communication module and a signal processor in a cochlear implant system according to some embodiments.

FIG. 6B is a schematic diagram illustrating exemplary electrical communication between an implantable battery and/or communication module and a signal processor in a cochlear implant system according to some embodiments. In the illustrated embodiment, the implantable battery and/or communication module 610 includes a signal generator 612 configured to output a signal through a lead (e.g., 190) to the signal processor 620. As described with respect to FIG. 6A, in some examples, the signal generator 612 is configured to generate both data and power signals (e.g., 650) for communication to the signal processor 620. In some embodiments, the signal generator 612 generates a digital signal for communication to the signal processor 620. The digital signal from the signal generator 612 can be communicated to the signal processor 620 at a particular clock rate. In some examples, the signals are generated at approximately 30 kHz. In various examples, data and power frequencies can range from approximately 100 Hz to approximately 10 MHz, and in some examples, may be adjustable, for example, by a user.

In the illustrated embodiment, the implantable battery and/or communication module 610 includes a controller in communication with the signal generator 612. In some examples, the controller is capable of adjusting communication parameters such as the clock rate of the signal generator 612. In an exemplary embodiment, the controller and/or the signal generator 612 can communicate with, for example, a patient's external programmer (e.g., as shown in FIG. 1). The controller and/or signal generator 612 can be configured to communicate data to the signal processor 620 (e.g., 651), such as updated firmware, signal processor 620 transfer functions, or the like.

As shown, the signal generator 612 outputs the generated signal to an amplifier 690 and an inverting amplifier 692. In some examples, both amplifiers are unity gain amplifiers. In some examples comprising digital signals, the inverting amplifier 692 can comprise a digital NOT gate. The output from the amplifier 690 and the inverting amplifier 692 are generally opposite one another and are directed to the signal processor 620. In some embodiments, the opposite nature of the signals output to the signal processor 620 from amplifiers 690 and 692 results in a charge-neutral communication between the implantable battery and/or communication module 610 and the signal processor 620, such that no net charge flows through the wearer.

In the illustrated example of FIG. 6B, the receiving circuitry in the signal processor 620 comprises a rectifier circuit 622 that receives signals (e.g., 650) from the amplifier 690 and the inverting amplifier 692. Since the output of one of the amplifiers 690 and 692 will be high, the rectifier circuit 622 can be configured to receive the opposite signals from the amplifiers 690 and 692 and generate therefrom a substantially DC power output 623. In various embodiments, the DC power 623 can be used to power a variety of components, such as the signal processor 620 itself, the middle ear sensor, the electrical and/or acoustic stimulator, or the like. The rectifier circuit 622 can include any known appropriate circuitry components for rectifying one or more input signals, such as a diode rectification circuit or a transistor circuit, for example.

As described elsewhere herein, the implantable battery and/or communication module 610 can communicate data to the signal processor 620. In some embodiments, the controller and/or the signal generator 612 is configured to encode the data for transmission via the output amplifiers 690 and 692. The signal processor 620 can include a signal extraction module 624 configured to extract the data signal 625 from the signal(s) (e.g., 650) communicated to the signal processor 620 to produce a signal for use by the signal processor 620. In some examples, the signal extraction module 624 is capable of decoding the signal that was encoded by the implantable battery and/or communication module 610. Additionally or alternatively, the signal extraction module 624 can extract a signal 625 resulting from the lead transfer function. In various examples, the extracted signal 625 can include, for example, an updated transfer function for the signal processor 620, a desired stimulation command, or other signals that affect operation of the signal processor 620.

In the illustrated example, the signal processor 620 includes a controller 626 that is capable of monitoring the DC power 623 and the signal 625 received from the implantable battery and/or communication module 610. The controller 626 can be configured to analyze the received DC power 623 and the signal 625 and determine whether or not the power and/or signal is sufficient. For example, the controller 626 may determine that the signal processor 620 is receiving insufficient DC power for stimulating a cochlear electrode according to the signal processor 620 transfer function, or that data from the implantable battery and/or communication module 610 is not communicated at a desired rate. Thus, in some examples, the controller 626 of the signal processor 620 can communicate with the controller 614 of the implantable battery and/or communication module 610 and provide feedback regarding the received communication. Based on the received feedback from the controller 626 of the signal processor 620, the controller 614 of the implantable battery and/or communication module 610 can adjust various properties of the signal output by the implantable battery and/or communication module 610. For example, the controller of the implantable battery and/or communication module 610 can adjust the clock rate of the communication from the signal generator 612 to the signal processor 620.

In some systems, the transmission efficiency between the implantable battery and/or communication module 610 and the signal processor 620 is dependent on the clock rate of transmission. Accordingly, in some examples, the implantable battery and/or communication module 610 begins by transmitting at an optimized clock rate until a change in clock rate is requested via the signal processor 620, for example, to enhance data transmission (e.g., rate, resolution, etc.). In other instances, if more power is required (e.g., the controller of the signal processor 620 determines the DC power is insufficient), the clock rate can be adjusted to improve transmission efficiency, and thus the magnitude of the signal received at the signal processor 620. It will be appreciated that in addition or alternatively to adjusting a clock rate, adjusting an amount of power transmitted to the signal processor 620 can include adjusting the magnitude of the signal output from the signal generator 612. In some embodiments, for example, with respect to FIGS. 6A-B, power and data can be communicated, for example, from implantable battery and/or communication module 610 to the signal processor 620 at a rate of approximately 30 kHz, and can be adjusted from there as necessary and/or as requested, for example, by the signal processor 620.

Figure 7A:
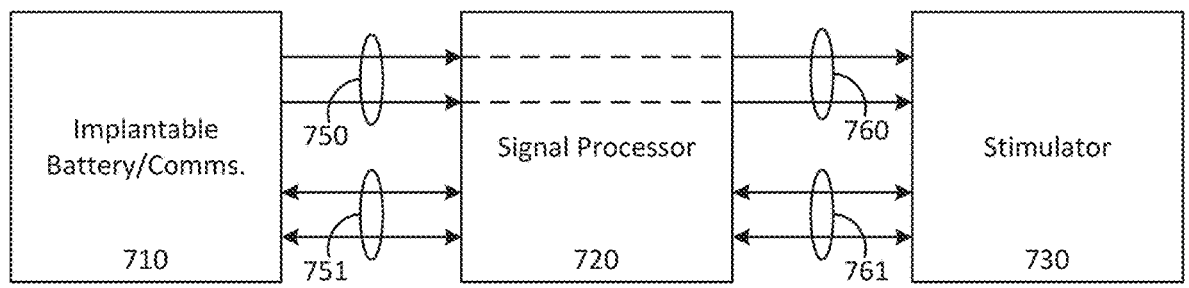
FIG. 7A is an alternative high-level schematic diagram illustrating an exemplary communication configuration between an implantable battery and/or communication module, a signal processor, and a stimulator.

FIG. 7A is an alternative high-level schematic diagram illustrating an exemplary communication configuration between an implantable battery and/or communication module, a signal processor, and a stimulator. In the example of FIG. 7A, the implantable battery and/or communication module 710 provides signals (e.g., 750) to the signal processor 720 via a first communication link and is further in two-way communication for providing additional signals (e.g., 751) with the signal processor 720. In the example of FIG. 7A, the implantable battery and/or communication module 710 can provide power signals (e.g., 750) to the signal processor 720 via a communication link and otherwise be in two-way data communication (751) with the signal processor 720 via a second communication link. In some such examples, the power (750) and data (751) signals can each include digital signals. However, in some embodiments, the power and data signals are transmitted at different clock rates. In some examples, the clock rate of the data signals is at least one order of magnitude greater than the clock rate of the power signals. For example, in an exemplary embodiment, the power signal is communicated at a clock rate of approximately 30 kHz, while the data communication occurs at a clock rate of approximately 1 MHz. Similarly to the embodiment described in FIG. 6A, in some examples, the clock rate can be adjustable, for example, via the implantable battery and/or communication module 710.

As described with respect to FIG. 6A, in some embodiments, the signal processor 720 can communicate information to the implantable battery and/or communication module 710, for example, feedback information and/or requests for more power, etc. (e.g., data signals 751). The implantable battery and/or communication module 710 can, in response, adjust the power and/or data output to the signal processor 720 (e.g., an amplitude, duty cycle, clock rate, etc.) in order to accommodate for the received feedback (e.g., to provide more power, etc.).

In some embodiments, similar communication can be implemented between the signal processor 720 and the stimulator 730, wherein the signal processor 720 provides power and data to the stimulator 730 and receives data in return from the stimulator 730. For example, the signal processor 720 can be configured to output signals power signals (e.g., 760) and data signals (e.g., 761) to the stimulator 730 (e.g., based on received inputs from a middle ear sensor or other device). Such communication can be implemented via a similar communication protocol as implemented between the implantable battery and/or communication module 710 and the signal processor 720. In some examples, the power signals provided to the stimulator 730 (e.g., 760) are the same signals (e.g., 750) received by the signal processor 720 from the implantable battery and/or communication module 710. Additionally, in some embodiments, the stimulator 730 can be configured to provide feedback signals to the signal processor 720 (e.g., 761), for example, representative of an executed stimulation process.

Figure 7B:
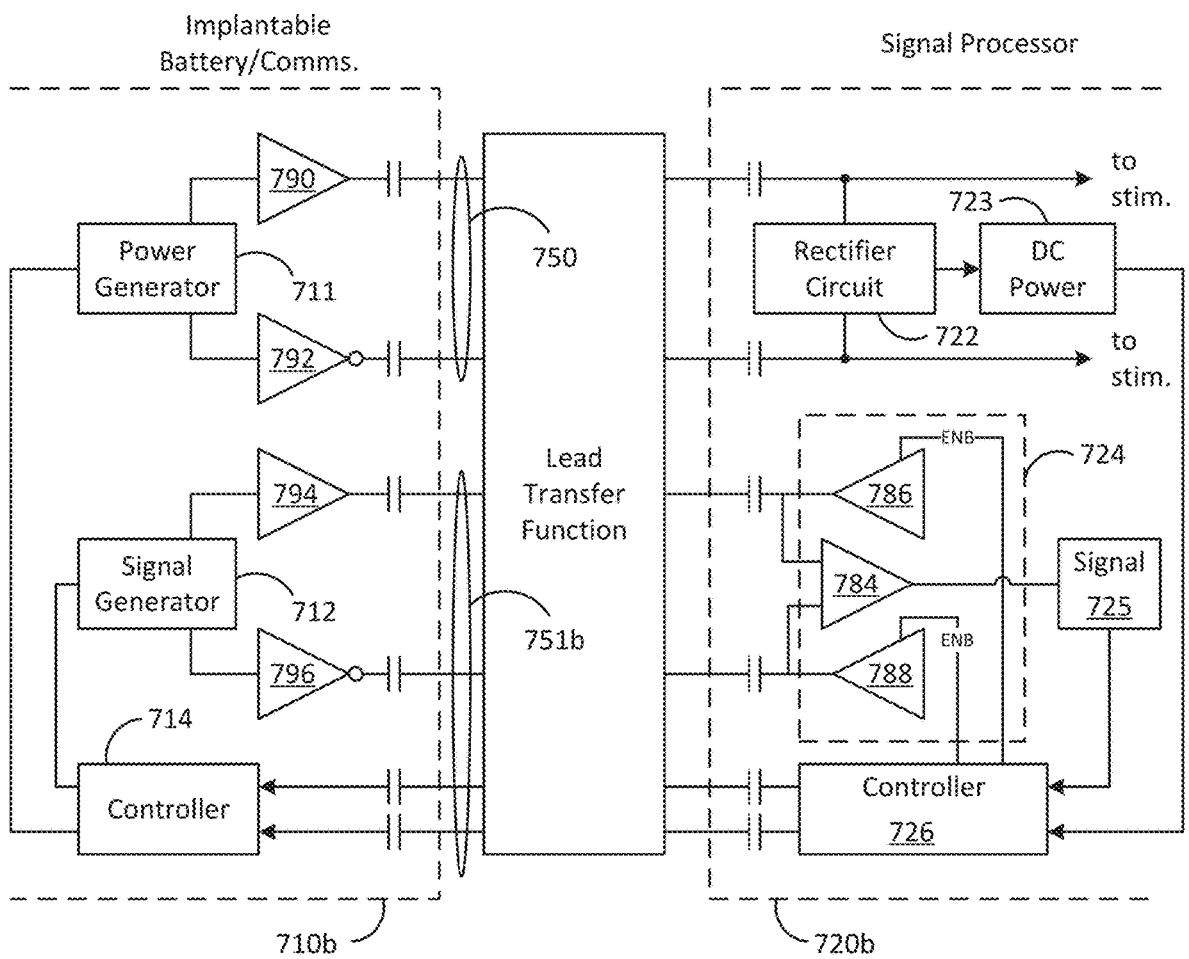
FIG. 7B is an alternative schematic diagram illustrating exemplary electrical communication between an implantable battery and/or communication module and a signal processor in a cochlear implant system similar to that shown in FIG. 7A.

FIG. 7B is an alternative schematic diagram illustrating exemplary electrical communication between an implantable battery and/or communication module 710b and a signal processor 720b in a cochlear implant system similar to that shown in FIG. 7A. In the illustrated embodiment of FIG. 7B, the implantable battery and/or communication module 710b includes a power signal generator 711 and a separate signal generator 712. The power signal generator 711 and signal generator 712 are each configured to output a signal through a lead (e.g., 190) to the signal processor 720b. In some embodiments, the power signal generator 711 and the signal generator 712 each generates digital signal for communication to the signal processor 720b. In some such embodiments, the digital signal (e.g., 750) from the power signal generator 711 can be communicated to the signal processor 720b at a power clock rate, while the digital signal (e.g., 751b) from the signal generator 712 can be communicated to the signal processor 720b at a data clock rate that is different from the power clock rate. For instance, in some configurations, power and data can be communicated most effectively and/or efficiently at different clock rates. In an exemplary embodiment, the power clock rate is approximately 30 kHz while the data clock rate is approximately 1 MHz. Utilizing different and separately communicated power and data signals having different clock rates can increase the transfer efficiency of power and/or data from the implantable battery and/or communication module 710b to the signal processor 720b.

In the illustrated embodiment, the implantable battery and/or communication module 710b includes a controller 714 in communication with the power signal generator 711 and the signal generator 712. In some examples, the controller 714 is capable of adjusting communication parameters such as the clock rate or content of the signal generator 712 and/or the power signal generator 711. In an exemplary embodiment, the controller 714 and/or the signal generator 712 or power signal generator 711 can communicate with, for example, a patient's external programmer (e.g., as shown in FIG. 1). The controller 714 and/or signal generator 712 can be configured to communicate data to the signal processor 720b, such as updated firmware, signal processor 720b transfer functions, or the like. Additionally or alternatively, the controller 714 can be configured to transmit signals such as audio or other signals streamed or otherwise received from one or more external devices as described elsewhere herein.

As shown, and similar to the example shown in FIG. 6B, the power signal generator 711 outputs the generated signal to an amplifier 790 and an inverting amplifier 792. In some examples, both amplifiers are unity gain amplifiers. In some examples comprising digital signals, the inverting amplifier 792 can comprise a digital NOT gate. The output from the amplifier 790 and the inverting amplifier 792 are generally opposite one another and are directed to the signal processor 720b. In the illustrated example, the receiving circuitry in the signal processor 720b comprises a rectifier circuit 722 that receives signals from the amplifier 790 and the inverting amplifier 792. Since the output of one of the amplifiers 790 and 792 will be high, the rectifier circuit 722 can be configured to receive the opposite signals from the amplifiers 790 and 792 and generate therefrom a substantially DC power output 723.

In various embodiments, the DC power 723 can be used to power a variety of components, such as the signal processor 720b itself, the middle ear sensor, the electrical and/or acoustic stimulator 730, or the like. The rectifier circuit 722 can include any known appropriate circuitry components for rectifying one or more input signals, such as a diode rectification circuit or a transistor circuit, for example. In some embodiments, signals from the power signal generator 711 are generated at a clock rate that is optimal for transmitting power through the lead (e.g., approximately 30 kHz). In the illustrated example of FIG. 7B, the rectifier circuit 722 can be arranged in parallel with power lines that are configured to communicate power signals to other components within the system, such as the stimulator 730, for example. For instance, in some embodiments, the same power signal (e.g., 750) generated from the power signal generator 711 and output via amplifiers 790 and 792 can be similarly applied to the stimulator 730. In some such examples, the stimulator 730 includes a rectifier circuit 722 similar to the signal processor 720b for extracting DC power from the power signal and the inverted power signal provided by amplifiers 790 and 792, respectively. In alternative embodiments, the signal processor 720b can similarly provide signals from a separate power signal generator 711 to provide power signals (e.g., at approximately 30 kHz) to the stimulator 730 similar to how power is provided from the implantable battery and/or communication module 710b to the signal processor 720b in FIG. 7B.

In the example of FIG. 7B, the signal generator 712 outputs a data signal (e.g., 751b) to an amplifier 794 and an inverting amplifier 796. In some examples, both amplifiers are unity gain amplifiers. In some examples comprising digital signals, the inverting amplifier 796 can comprise a digital NOT gate. The output from the amplifier 794 and the inverting amplifier 796 are generally opposite one another and are directed to the signal processor 720b.

As described elsewhere herein, in some embodiments, the controller 714 and/or the signal generator 712 is configured to encode data for transmission via the output amplifiers 794 and 796. The signal processor 720b can include a signal extraction module 724 configured to extract the data from the signal(s) 725 communicated to the signal processor 720b to produce a signal 725 for use by the signal processor 720b. In some examples, the signal extraction module 724 is capable of decoding the signal that was encoded by the implantable battery and/or communication module 710b. Additionally or alternatively, the signal extraction module 724 can extract a resulting signal 725 resulting from the lead transfer function. In various examples, the extracted signal can include, for example, an updated transfer function for the signal processor 720b, a desired stimulation command, or other signals that affect operation of the signal processor 720b.

In the example of FIG. 7B, the signal extraction module 724 includes a pair of tri-state buffers 786 and 788 in communication with signals output from the signal generator 712. The tri-state buffers 786 and 788 are shown as having "enable" (ENB) signals provided by controller 726 in order to control operation of the tri-state buffers 786 and 788 for extracting the signal from the signal generator 712. Signals from the signal generator 712 and buffered by tri-state buffers 786 and 788 are received by amplifier 784, which can be configured to produce a signal 725 representative of the signal generated by the signal generator 712.

In some examples, communication of signals generated at the signal generator 712 can be communicated to the signal processor 720b at a clock rate that is different from the clock rate of the signals generated by the power signal generator 711. For instance, in some embodiments, power signals from the power signal generator 711 are transmitted at approximately 30 kHz, which can be an efficient frequency for transmitting power. However, in some examples, the signals from the signal generator 712 are transmitted at a higher frequency than the signal from the power signal generator 711, for example, at approximately 1 MHz. Such high frequency data transmission can be useful for faster data transfer than would be available at lower frequencies (e.g., the frequencies for transmitting the signal from the power signal generator 711). Thus, in some embodiments, power and data can be communicated from the implantable battery and/or communication module 710b to the signal processor 720b via different communication channels at different frequencies.

Similar to the embodiment shown in FIG. 6B, in the illustrated example of FIG. 7B, the signal processor 720b includes a controller 726 that is in communication with the implantable battery and/or communication module 710b. In some such embodiments, the controller 726 in the signal processor 720b is capable of monitoring the DC power 723 and/or the signal 725 received from the implantable battery and/or communication module 710b. The controller 726 can be configured to analyze the received DC power 723 and the signal 725 and determine whether or not the power and/or signal is sufficient. For example, the controller 726 may determine that the signal processor 720b is receiving insufficient DC power for stimulating a cochlear electrode according to the signal processor 720b transfer function, or that data from the implantable battery and/or communication module 710b is not communicated at a desired rate. Thus, in some examples, the controller 726 of the signal processor 720b can communicate with the controller 714 of the implantable battery and/or communication module 710b and provide feedback regarding the received communication. Based on the received feedback from the controller 726 of the signal processor 720b, the controller 714 of the implantable battery and/or communication module 710b can adjust various properties of the signals output by the power signal generator 711 and/or the signal generator 712.

In the illustrated example of FIG. 7B, bidirectional communication signals 751b between the implantable battery and/or communication module 710b and signal processor 720b comprises signals from the amplifiers 794 and 796 in one direction, and communication from controller 726 to controller 714 in the other direction. It will be appreciated that a variety of communication protocols and techniques can be used in establishing bidirectional communication signals 751b between the implantable battery and/or communication module 710b and signal processor 720b.

For example, in some embodiments, the implantable battery and/or communication module 710b need not include amplifiers 794 and 796, and instead transmits a signal and not its inverse to the signal processor 720b. In other examples, the signal processor includes amplifiers similar to 794 and 796, and outputs a signal and its inverse back to the implantable battery and/or communication module 710b. Additionally or alternatively, in some embodiments, the signal generator 712 can be integral with the controller 714 and/or the signal extraction module 724 can be integral with controller 726, wherein controllers 714 and 726 can be in bidirectional communication via signal generator 712 and/or the signal extraction module 724. In general, the implantable battery and/or communication module 710b and the signal processor 720b can be in bidirectional communication for communicating data signals separate from the power signals provided by power signal generator 711.

As described, separate communication channels for power (e.g., 750) and data (e.g., 751b) can be used for providing both power and data from the implantable battery and/or communication module 710b and the signal processor 720b. This can allow for separate data and power clocking rates in order to improve the power transmission efficiency as well as the data transmission efficiency and/or rate. Moreover, in some examples, if the bidirectional communication (e.g., 751b) between the implantable battery and/or communication module 710b and the signal processor 720b fails (e.g., due to component failure, connection failure, etc.), data for communication from the implantable battery and/or communication module 710b can be encoded in the power signals (e.g., 750) from the power signal generator 711 and transmitted to the signal processor 720b. Thus, similar to the embodiment described with respect to FIG. 6B, both power and data can be transmitted via the same signal.

In some examples, the signal extraction module 724 can be configured to receive data received from the power signal generator 711, for example, via an actuatable switch that can be actuated upon detected failure of communication 751b. In other examples, the signal extraction module 724 and/or the controller 726 can generally monitor data from the power signal generator 711 and identify when signals received from the power signal generator 711 include data signals encoded into the received power signal in order to determine when to consider the power signals to include data.

Accordingly, in some embodiments, the configuration of FIG. 7B can be implemented to establish efficient, bidirectional communication between the implantable battery and/or communication module 710b and the signal processor 720b. Failure in bidirectional communication 751b can be identified manually and/or automatically. Upon detection of failure in the bidirectional communication 751b, the controller 714 can encode data into the power signal output from the power signal generator 711, and power and data can be combined into a single signal such as described with respect to FIG. 6B.

Figure 7C:
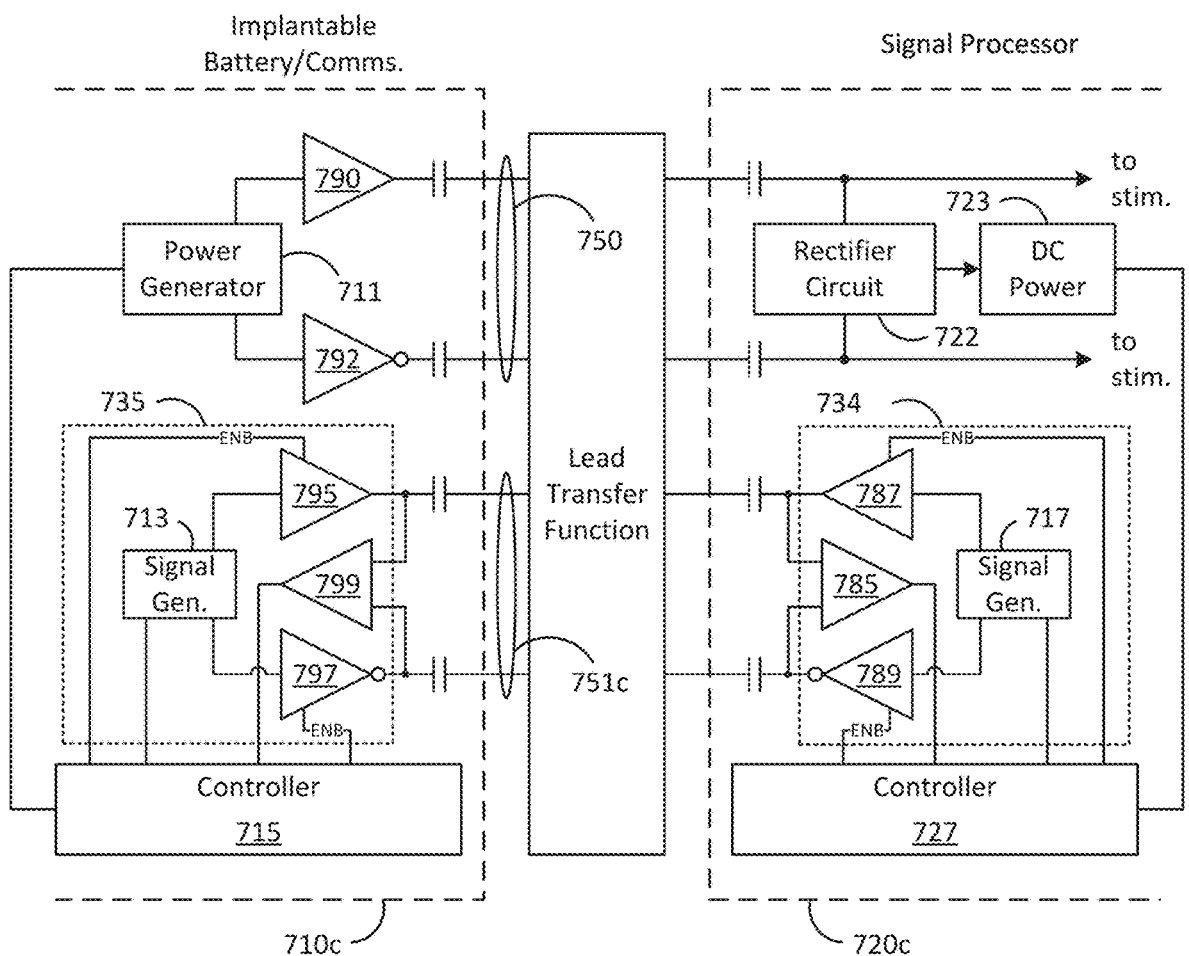
FIG. 7C is another alternative schematic diagram illustrating exemplary electrical communication between an implantable battery and/or communication module and a signal processor in a cochlear implant system similar to that shown in FIG. 7A.

FIG. 7C is another alternative schematic diagram illustrating exemplary electrical communication between an implantable battery and/or communication module 710c and a signal processor 720c in a cochlear implant system similar to that shown in FIG. 7A. Similar to the embodiment of FIG. 7B, in the illustrated embodiment of FIG. 7C, the implantable battery and/or communication module 710c includes a power signal generator 711 configured to output a signal through a lead (e.g., 190) to the signal processor 720c. In some embodiments, the power signal generator 711 generates a digital signal (e.g., 750) for communication to the signal processor 720c, for example, at a power clock rate. The power signal generator 711 and corresponding amplifiers 790, 792, as well as rectifier circuit 722, can operate similar to described with respect to FIG. 7B in order to extract DC power 723 and, in some examples, output power signals to further system components, such as stimulator 730.

In the illustrated embodiment, the implantable battery and/or communication module 710c includes a signal generator 713, which can be capable of providing data signals to the signal processor. In some embodiments, the signal generator 713 generates a digital signal for communication to the signal processor 720c. In some such embodiments, the digital signal (e.g., 751c) from the signal generator 713 can be communicated to the signal processor 720b at a data clock rate that is different from the power clock rate. For instance, as described elsewhere herein, in some configurations, power and data can be communicated most effectively and/or efficiently at different clock rates. In an exemplary embodiment, the power clock rate is approximately 30 kHz while the data clock rate is approximately 1 MHz. Utilizing different and separately communicated power and data signals having different clock rates can increase the transfer efficiency of power and/or data from the implantable battery and/or communication module 710c to the signal processor 720c.

The embodiment of FIG. 7C includes a controller 715 in communication with the power signal generator 711 and the signal generator 713. In some examples, the controller 715 is capable of adjusting communication parameters such as the clock rate or content of the signal generator 713 and/or the power signal generator 711. In an exemplary embodiment, the controller 715 and/or the signal generator 713 or power signal generator 711 can communicate with, for example, a patient's external programmer (e.g., as shown in FIG. 1). The controller 715 and/or signal generator 713 can be configured to communicate data to the signal processor 720c, such as updated firmware, signal processor 720c transfer functions, or the like.

Similar to the example in FIG. 7B, in the example of FIG. 7C, the signal generator 713 outputs a data signal (e.g., 751) to an amplifier 795 and an inverting amplifier 797. In some examples, both amplifiers are unity gain amplifiers. In some examples, amplifiers 795, 797 comprise tri-state buffers. In some examples comprising digital signals, the inverting amplifier 797 can comprise a digital NOT gate. The output from the amplifier 795 and the inverting amplifier 797 are generally opposite one another and are directed to the signal processor 720c.

As described elsewhere herein, in some embodiments, the controller 715 and/or the signal generator 713 is configured to encode data for transmission via the amplifiers 795 and 797. The signal processor 720c can include a signal extraction module 734 configured to extract the data from the signal(s) communicated to the signal processor 720c to produce a signal for use by the signal processor 720c. In some examples, the signal extraction module 734 is capable of decoding the signal that was encoded by the implantable battery and/or communication module 710c. Additionally or alternatively, the signal extraction module 734 can extract a signal resulting from the lead transfer function. In various examples, the extracted signal can include, for example, an updated transfer function for the signal processor 720c, a desired stimulation command, or other signals that affect operation of the signal processor 720c.

In the example of FIG. 7C, similar to signal extraction module 724 in FIG. 7B, the signal extraction module 734 includes a pair of tri-state buffers 787 and 789 in communication with signals output from the signal generator 713. The tri-state buffers 787 and 789 are shown as having "enable" (ENB) signals provided by controller 727 in order to control operation of the tri-state buffers 787 and 789 for extracting the signal from the signal generator 713. Signals from the signal generator 713 and buffered by tri-state buffers 787 and 789 are received by amplifier 785, which can be configured to produce a signal representative of the signal generated by the signal generator 713.

As described elsewhere herein, in some examples, communication of signals generated at the signal generator 713 can be communicated to the signal processor 720c at a clock rate that is different from the clock rate of the signals generated by the power signal generator 711. For instance, in some embodiments, power signals from the power signal generator 711 are transmitted at approximately 30 kHz, which can be an efficient frequency for transmitting power. However, in some examples, the signals from the signal generator 713 are transmitted at a higher frequency than the signal from the power signal generator 711, for example, at approximately 1 MHz. Such high frequency data transmission can be useful for faster data transfer than would be available at lower frequencies (e.g., the frequencies for transmitting the signal from the power signal generator 711). Thus, in some embodiments, power and data can be communicated from the implantable battery and/or communication module 710c to the signal processor 720c via different communication channels at different frequencies.

In the illustrated example of FIG. 7C, the signal processor 720c includes a signal generator 717 and controller 727 that is in communication with the signal generator 717. Similar to the operation of signal generator 713 and amplifiers 795 and 799, the signal generator can be configured to produce output signals to buffers 787 and 789, which can be configured to output signals to the implantable battery and/or communication module 710c.

In some embodiments, the controller 727 in the signal processor 720c is capable of monitoring the DC power 723 and/or the signal received from the implantable battery and/or communication module 710c. The controller 726 can be configured to analyze the received DC power 723 and the signal and determine whether or not the power and/or signal is sufficient. For example, the controller 727 may determine that the signal processor 720c is receiving insufficient DC power for stimulating a cochlear electrode according to the signal processor 720c transfer function, or that data from the implantable battery and/or communication module 710c is not communicated at a desired rate. Thus, in some examples, the controller 727 of the signal processor 720c cause the signal generator 717 to generate communication signals to send to implantable battery and/or communication module 710c. Such signals can be used to provide feedback regarding signals received by the signal processor 720c, such as the DC power 723.

In the example of FIG. 7C, amplifiers 795 and 797 are shown as including tri-state amplifiers (e.g., tri-state buffers) controllable by the controller 727. Similar to the configuration in the signal processor 720c, the implantable battery and/or communication module 710c includes a signal extraction module 735 configured to extract data from the signal(s) communicated to the implantable battery and/or communication module 710c from signal generator 717 of the signal processor 720c. The signal extraction module 735 includes amplifiers 795 and 797 (e.g., tri-state buffers) in communication with signals output from the signal generator 717. Signals from the signal generator 717 and received at amplifiers 795 and 797 are received by amplifier 799, which can be configured to produce a signal representative of the signal generated by the signal generator 717 to controller 715 of the implantable battery and/or communication module 710. Thus, in some embodiments, the controller 727 of the signal processor 720c is configured to communicate data back to the implantable battery and/or communication module 710a via buffers 787 and 789.

As described with respect to other embodiments, based on the received feedback from the controller 727 of the signal processor 720c, the controller 715 of the implantable battery and/or communication module 710c can adjust various properties of the signals output by the power signal generator 711 and/or the signal generator 713.

Thus, in the illustrated example of FIG. 7C, bidirectional communication signal 751 between the implantable battery and/or communication module 710c and signal processor 720c includes communication between different signal extraction modules 735 and 734. As shown, both the implantable battery and/or communication module 710c and the signal processor 720c include a controller (715, 727) that communicates with a signal generator (713, 717) for producing output signals. The signal generator (713, 717) outputs signals via tri-state amplifiers, including one inverting amplifier (797, 789) for communication across bidirectional communication 751c for receipt by the other signal extraction module (734, 735).

Thus, in some embodiments, bidirectional communication 751c between the implantable battery and/or communication module 710c and the signal processor 720c can be enabled by each of the implantable battery and/or communication module and the signal processor receiving and transmitting data via approximately the same communication structure as the other. In some such examples, the implantable battery and/or communication module 710c and the signal processor 720c include signal extraction modules 735 and 734, respectively, configured both to output signals from a signal generator (e.g., via signal generator 713 or signal generator 717) and receive and extract signals (e.g., via amplifier 785 and amplifier 799).

In the example of FIG. 7C, amplifiers 795 and 797 comprise tri-state amplifiers that selectively (e.g., via "enable" control from controller 715) output the signal from signal generator 713, and amplifier 797 is shown as an inverting amplifier. As described, in some examples, amplifiers 795 and 797 comprise tri-state buffers. Similarly, of tri-state buffers 787 and 789 that selectively (e.g., via "enable" control from controller 727) output the signal from signal generator 717, buffer 789 is shown as an inverting amplifier. As described elsewhere herein, communicating a signal and its inverse (e.g., via 795 and 797) allows communication with no net charge flow between the implantable battery and/or communication module 710c and the signal processor 720c. Thus, bidirectional communication between the implantable battery and/or communication module 710c and the signal processor 720c can be performed without a net charge flow between the components.

As described elsewhere herein, power from power generator 711 and data from signal generator 713 (and/or signal generator 717) can be communicated at different clocking rates to optimize power and data transfer. In some examples, if data communication (e.g., via bidirectional communication 751c) fails, the controller 715 can be configured to control power generator 711 to provide both power and data signals via amplifiers 790 and 792, for example, as described with respect to FIG. 6B.

Accordingly, in some embodiments, the configuration of FIG. 7C can be implemented to establish efficient, bidirectional communication between the implantable battery and/or communication module 710 and the signal processor 720. Failure in bidirectional communication 751 can be identified manually and/or automatically. Upon detection of failure in the bidirectional communication 751, the controller 715 can encode data into the power signal output from the power signal generator 711, and power and data can be combined into a single signal such as described with respect to FIG. 6B.

As discussed elsewhere herein, different safety standards can exist regarding electrical communication within the patient's body. For example, safety standards can limit the amount of current that can safely flow through a patient's body (particularly DC current). As shown in FIGS. 6B, 7B, and 7C, each of the illustrated communication paths between the implantable battery and/or communication module and the signal processor are coupled to output capacitors. The capacitors positioned at the inputs and outputs of the implantable battery and/or communication module and the signal processor can substantially block DC current from flowing therebetween while permitting communication of AC signals.

As described elsewhere herein, in some embodiments, the data communicated between the implantable battery and/or communication module and the signal processor (e.g., from the signal generator) is encoded. In some such examples, the encoding can be performed according to a particular data encoding method, such as an 8b/10b encoding scheme, to achieve DC balance in the communicated signal. For example, in some embodiments, data is encoded such that the numbers of high and low bits communicated between components at each clock signal meet certain criteria to prevent a charge of a single polarity from building up on any of the capacitors. Such encoding can minimize the total charge that flows between the implantable battery and/or communication module and the signal processor during communication.

While described and illustrated as representing communication between the implantable battery and/or communication module and the signal processor, it will be appreciated that communication configurations such as shown in FIGS. 5A, 5B, 6A, 6B, 7A, 7B, and 7C can be implemented between any pair of devices generally in communication with one another. For example, isolating circuitry (e.g., $R_{Can}$) can be included in any of the system components (e.g., middle ear sensor, acoustic stimulator, electrical stimulator, etc.) to effectively isolate the ground signals from each component from its respective can. Similarly, the exemplary capacitive AC coupling with DC blocking capacitors and DC balancing encoding as described elsewhere herein can be incorporated as the communication interface between any two communicating components.

As described, data can be communicated from the implantable battery and/or communication module to the signal processor for a variety of reasons. In some examples, data is that communicated to the implantable battery and/or communication module from an external device, such as a programmer as shown in FIG. 1. In an exemplary process, a programmer, such as a clinician's computer, can be used to communicate with a patient's fully implanted system via a communication configuration such as shown in FIGS. 6B, 7B, or 7C. For example, a programmer can communicate wirelessly (e.g., via Bluetooth or other appropriate communication technique) with the patient's implantable battery and/or communication module. Signals from the programmer can be sent from the implantable battery and/or communication module to the signal processor via the communication configurations of FIGS. 6B, 7B, or 7C.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

In some embodiments, various internal properties of the system may be tested. For instance, various impedance values, such as a sensor impedance or a stimulator impedance can be tested such as described in U.S. Patent Publication No. 2015/0256945, entitled TRANSDUCER IMPEDANCE MEASUREMENT FOR HEARING AID, which is assigned to the assignee of the instant application, the relevant portions of which are incorporated by reference herein.

Figure 7D:
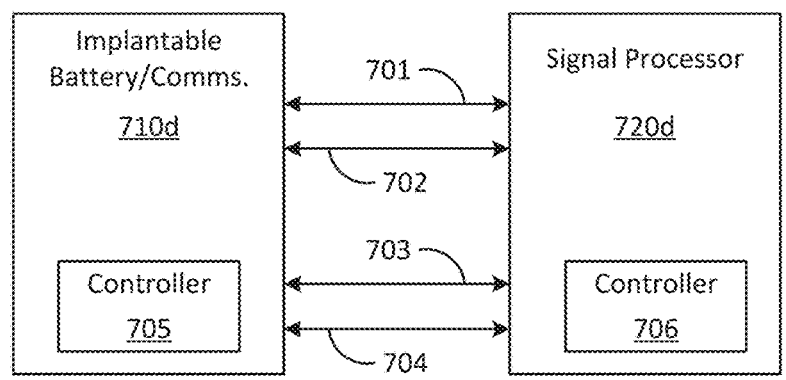
FIG. 7D is high-level schematic diagram illustrating exemplary electrical communication between an implantable battery and/or communication module and a signal processor in a cochlear implant system similar to that shown in FIG. 7A.

Additionally or alternatively, various characteristics of individual leads can be analyzed. FIG. 7D is high-level schematic diagram illustrating exemplary electrical communication between an implantable battery and/or communication module and a signal processor in a cochlear implant system similar to that shown in FIG. 7A. In the simplified example of FIG. 7D, conductors 701, 702, 703, and 704 extend between implantable battery and/or communication module 710$d$ and signal processor 720$d$. In some examples, such conductors are included in a lead (e.g., lead 190) extending between the implantable battery and/or communication module 710$d$ and signal processor 720$d$. In the example of FIG. 7D, implantable battery and/or communication module 710$d$ includes controller 705 and signal processor 720$d$ includes controller 706. Other internal components of the implantable battery and/or communication module 710$d$ and signal processor 720$d$ are not shown, though various configurations are possible, such as shown in FIGS. 6B, 7B, or 7C.

In some embodiments, one or both of controllers 705, 706 can be configured to apply a test signal to one or more of conductors 701, 702, 703, 704 in order to test one or more properties of such conductors. In an exemplary test process, a controller (e.g., 705) can drive a signal (e.g., a sine wave or other shaped wave) across a conductor (e.g., 701) and measure the sent current and the voltage at which the current is sent. From this information, the controller can determine conductor impedance, including integrity of the conductor (e.g., whether or not the conductor is broken). Similarly, a controller can be configured to ground a second conductor (e.g., 702) while driving the test signal across a test conductor (e.g., 701) in order to measure one or more electrical parameters between the two conductors (e.g., capacitance, impedance, etc.).

During exemplary operation, a controller can be configured to apply a test signal to a first conductor (e.g., 701) and ground a second conductor (e.g., 702). The controller can be configured to apply a test signal at a plurality of frequencies (e.g., perform a frequency sweep) and measure impedance vs. frequency between the first conductor and the second, grounded conductor. In various examples, a controller can be configured to perform such tests using any two conductors 701, 702, 703, 704, to test for baseline values (e.g., when the system is in a known working condition) or to test for expected values (e.g., to compare to an established baseline). In different embodiments, the controller in the implantable battery and/or communication module 710$d$ (controller 705) and/or the controller in the signal processor 720$d$ (controller 706) can perform the grounding of one or more conductors and/or apply the test signal to one or more conductors.

In some embodiments, such test processes can be performed automatically, for example, according to a programmed schedule. Additionally or alternatively, such test processes can be initiated manually, for example, by a wearer or a clinician, via an external device such as via a programmer (e.g., 100) or charger (e.g., 102). The results of such processes can be stored in an internal memory for later access and analysis, and/or can output to an external device for viewing. In some examples, results and/or a warning can be output to an external device automatically in the event that one or more results deviates sufficiently from a baseline value. In various examples, sufficient variation from the baseline for triggering an output can be based on a percent variation from the baseline (e.g., greater than 1% deviation from be baseline, greater than 5% deviation, greater than 10% deviation, etc.). Additionally or alternatively, sufficient variation an include varying a certain number of standard deviations from the baseline (e.g., greater than one standard deviation, two standard deviations, etc.). In various embodiments, the amount of variation that triggers outputting the results and/or a warning is adjustable. Additionally or alternatively, such an amount can vary between different measurements.

In some embodiments, one or more actions may be performed in response to the results of such an analysis. For instance, in an exemplary embodiment described with respect to FIG. 7B, if a test reveals an unexpected impedance on one of the signal conductors (e.g., from amplifier 794 or inverting amplifier 796), such as an open circuit, the controller 714 may be configured to change operation of the system. For instance, controller 714 can be configured to adjust the output from power generator 711 in order to provide both power and data signals from the power generator 711, such as described with respect to the configuration in FIG. 6B. In some examples, the controller 714 can be configured to transmit a signal to an external device signaling such a change in operation and/or alerting a wearer and/or clinician that one or more conductors may be damaged or otherwise not operational.

While shown in several embodiments (e.g., FIGS. 1, 4, 6A, 7A) as being separate components connected by a lead (e.g., lead 180), in some examples, the processor (e.g., 120) and the stimulator (e.g., 130) can be integrated into a single component, for example, within a hermetically sealed housing. Some such embodiments are described in U.S. patent application Ser. No. 16/797,388, filed Feb. 21, 2020, and which is assigned to the assignee of the instant application and is incorporated herein by reference.

As described elsewhere herein, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function.

Figure 8:
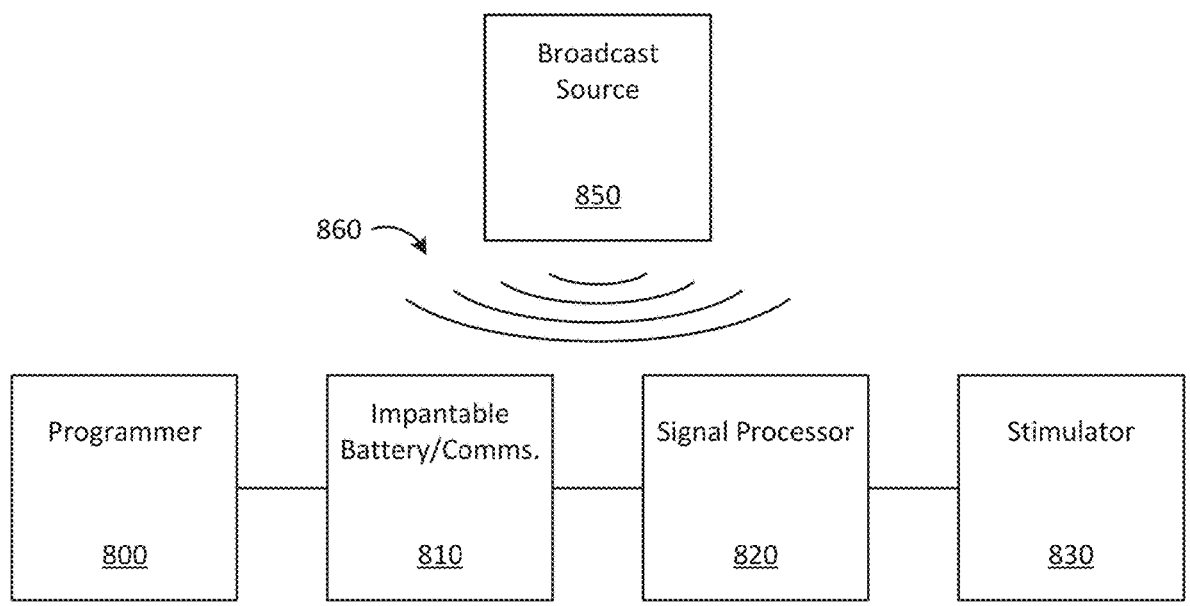
FIG. 8 is a process flow diagram illustrating an exemplary process for establishing a preferred transfer function for a patient.

Additionally or alternatively, one or more system components can be configured to receive broadcast signals for converting into stimulation signals. FIG. 8 is a schematic system diagram showing an implantable system configured to receive broadcast signals from a broadcast device. As shown in the example of FIG. 8, a broadcast source 850 broadcasts a signal via communication link 860. The communication link 860 can include communication via a variety of communication protocols, such as Wi-Fi, Bluetooth, or other known data transmission protocols. Broadcast source 850 can include any of a variety of components, such as a media source (e.g., television, radio, etc.), communication device (e.g., telephone, smartphone, etc.), a telecoil or other broadcast system (e.g., at a live performance), or any other source of audio signals that can be transmitted to an implanted system or to an external device of an implanted system (e.g., a system programmer, etc.).

An implantable system including a programmer 800, an implantable battery and/or communication module 810, a signal processor 820, and a stimulator 830 can generally receive the data from the broadcast source 850 via communication link 860. In various embodiments, any number of components in the implantable system can include a receiving device, such as a telecoil, configured to receive broadcast signals for eventual conversion into stimulation signals.

For instance, in some embodiments, programmer 800 can include a telecoil relay configured to receive broadcast telecoil signals from a broadcast source 850. The programmer can be configured to subsequently communicate a signal representative of the received broadcast signal to the implantable battery and/or communication module 810 and/or the signal processor 820, e.g., via a Bluetooth communication. If the communication is received from the programmer 800 via the implantable battery and/or communication module 810, the implantable battery and/or communication module 810 can communicate the signal to the signal processor, for example, as described in any of FIGS. 6A, 6B, 7A, or 7C.

In some such embodiments, the signal processor 820 can be configured to receive such signals from the implantable battery and/or communication module 810 and output stimulation signals to the stimulator 830 based on the received signals and the signal processor transfer function. In other examples, the signal processor 820 can include a telecoil relay or other device capable of receiving broadcast signals from the broadcast source 850. In some such embodiments, the signal processor 820 processes the received signals according to the signal processor transfer function and outputs stimulations signals to the stimulator 830.

In some embodiments, the signal processor 820 can be in communication with a plurality of input sources, such as, for example, a combination of an implanted microphone, a middle ear sensor, and a broadcast source 850 (e.g., via the implantable battery and/or communication module 810). In some such examples, the signal processor can be programmed with a plurality of transfer functions, each according to respective input sources. In such embodiments, the signal processor can identify which one or more input sources are providing input signals and process each such input signal according to the transfer function associated with its corresponding input source.

In some examples, a signal processor 820 receiving a plurality of input signals from a corresponding plurality of input sources effectively combines the signals when producing a stimulation signal to the stimulator 830. That is, in some embodiments, input sources are combined to form the stimulation signal from the signal processor 820. In some such examples, a user may be able to mix the various received input signals in any way desired. For example, a user may choose to blend a variety of different input streams, such as an input from a middle ear sensor or other implanted device, a signal received from an external device (e.g., a telecoil relay, a Bluetooth connection such as to a smartphone, etc.), and the like. In an exemplary configuration, a user may elect to equally blend two input sources such that the stimulation signal is based 50% on a first input source and 50% on a second input source.

Additionally or alternatively, a user may elect to effectively "mute" one or more input sources so that the signal processor 820 outputs stimulations signals based on input signals received from unmuted sources. Similarly, a user may be able to select a single source from which to process received input signals. For example, in some embodiments, a user may select to have signals received from broadcast source 850 processed and converted into stimulation signals while having signals received from, for example, a middle ear sensor, disregarded.

In some examples, direct communication with the signal processor can be used to test the efficacy of a given signal processor transfer function and associated stimulation (e.g., acoustic or electrical) parameters. For example, the programmer can be used to disable input signals from a middle ear sensor or other input source and provide a customized signal to the signal processor to simulate a signal from the input source. The signal processor processes the received signal according to its transfer function and actuates the electrical stimulator and/or the acoustic stimulator accordingly. The processor can be used to test a variety of customized "sounds" to determine the efficacy of the signal processor transfer function for the given patient for each "sound."

Various features and functions of implantable systems have been described herein. As described, in various embodiments, system operation(s) can be adjusted based on communication with the implanted system from components located outside of the body while the system remains implanted. In some embodiments, the system may include any number of external devices capable of interfacing with the system in a variety of ways.

Figure 9:
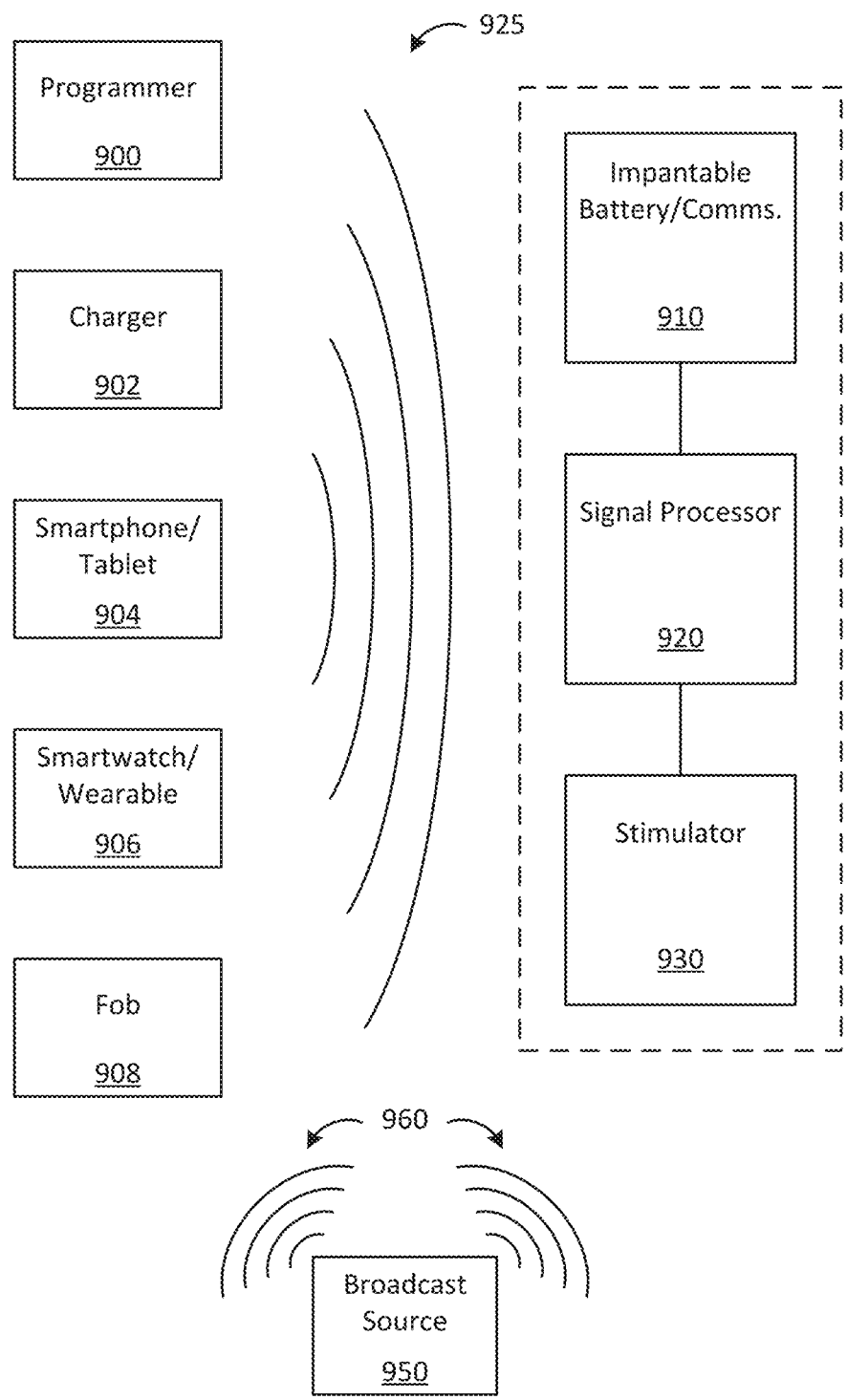
FIG. 9 is a schematic diagram illustrating possible communication between a variety of system components according to some embodiments of a fully implantable system.

FIG. 9 is a schematic diagram illustrating possible communication between a variety of system components according to some embodiments of a fully implantable system. In the illustrated embodiment, implanted components (outlined in broken line) of a system include an implantable battery and/or communication module 910, a signal processor 920, and a stimulator 930. Such implanted components can operate according to various examples as described herein in order to effectively stimulate a user (e.g.., via electrical and/or acoustic stimulation) in response to received input signals.

The schematic illustration of FIG. 9 includes a plurality of external devices capable of wirelessly interfacing with one or more of the implanted components, for example, via communication link 925. Such devices can include a programmer 900, a charger 902, a smartphone/tablet 904, a smartwatch or other wearable technology 906, and a fob 908. In some examples, such components can communicate with one or more implantable components via one or more communication protocols via wireless communication link 925, such as Bluetooth, Zigbee, or other appropriate protocols. In various embodiments, different external devices are capable of performing one or more functions associated with system operation. In some such embodiments, each external device is capable of performing the same functions as the others. In other examples, some external devices are capable of performing more functions than others.

For example, a programmer 900 can be capable of interfacing wirelessly with one or more implantable components in order to control a variety of operating parameters of the implanted system. For example, in some embodiments, programmer 900 can be configured to adjust a signal processor transfer function or select an operating profile (e.g., associated with a particular signal processor transfer function according to a particular user, environment, etc.). In some examples, the programmer 900 can be used to establish user profiles, such as preferred signal processor transfer functions, as described elsewhere herein. The programmer 900 can additionally or alternatively be used to turn the system on or off, adjust the volume of the system, receive and stream input data to the system (e.g., the implantable battery and/or communication module 910). In some embodiments, the programmer 900 includes a display for displaying various information to the user. For example, the display can be used to indicate a mode of operation (e.g., a loaded user profile), a remaining power level, or the like. In some such embodiments, the display can function as a user interface by which a user can adjust one or more parameters, such as volume, profile, input source, input mix, and the like.

In some embodiments, a charger 902 can be used to charge one or more internal batteries or other power supplies within the system, such as in the implantable battery and/or communication module 910. In some examples, the charger 902 can include the same functionality as the programmer 900, including, for instance, a display and/or user interface. In some such embodiments, the programmer 900 and the charger 902 can be integrated into a single device.

In some embodiments, various external devices such as a smartphone or tablet 904 can include an application ("app") that can be used to interface with the implanted system. For example, in some embodiments, a user may communicate (e.g., via link 925) with the system via the smartphone or tablet 904 in order to adjust certain operating factors of the system using a predefined app to provide an interface (e.g., a visual interface via a display integrated into the external device). The app can assist the user in adjusting various parameters, such as volume, operating profile, on/off, or the like. In some examples, the smartphone/tablet 904 can be used to stream input signals to the implanted system, such as media or communication playing on the smartphone/tablet 904.

In some systems, a smartwatch or other wearable technology 906 can interact with the system in a similar way as the smartphone/tablet 904. For example, the smartwatch or other wearable technology 906 can include an app similar to that operable on the smartphone/tablet to control operation of various aspects of the implanted system, such as volume control, on/off control, etc.

In some embodiments, the fob 908 can be used to perform basic function with respect to the implanted system. For instance, in some embodiments, a fob 908 can be used to load/implement a particular operating profile associated with the fob 908. Additionally or alternatively, the fob 908 can function similar to the shut-off controller 104 of FIG. 1 and can be used to quickly disable and/or mute the system. As described elsewhere herein, in some examples, the same device used to disable and/or mute the system (e.g., fob 908) can be used to enable and/or unmute the system.

The schematic diagram of FIG. 9 further includes a broadcast source 950 configured to broadcast signals 960 that are receivable via one or more external devices and/or one or more implanted system components. Similar to the broadcast source 850 in FIG. 8, broadcast source 950 can be configured to emit signals that can be turned into stimulation signals for application by stimulator 930. Broadcast signals 960 can include, for example, telecoil signals, Bluetooth signals, or the like. In various embodiments, one or more external devices, such as a programmer 900, charger 902, smartphone/tablet 904, smartwatch/wearable device 906, and/or fob 908 can include a component (e.g., a telecoil relay) capable of receiving broadcast signal 960. The external device(s) can be further configured to communicate a signal to one or more implanted components representative of the received broadcast signal 960 for applying stimulation to the patient based on the broadcast signal 960.

Additionally or alternatively, in some embodiments, one or more implanted system components, such as an implantable battery and/or communication module 910, a signal processor 920, and/or a stimulator 930 can be configured to receive broadcast signals 960. Such component(s) can be used to generate stimulation signals for applying to a user via stimulator 930 according to the received broadcast signals 960.

As described, in some embodiments, various devices can communicate with components in an implanted system via wireless communication protocols such as Bluetooth. Various data and signals can be communicated wirelessly, including control signals and streaming audio. However, in some cases, such wireless communication should be made secure so that a system only communicates with those devices desired by the wearer. This can prevent unwanted signals from being broadcast to an implanted device and/or unauthorized access to one or more adjustable device settings.

In some embodiments, one or more implanted system components comprises a near field communication component configured to facilitate communication between the system and an external device only when brought into very close proximity to the near field communication component. In some such examples, once near-field communication is established, the pairing for longer-range wireless communication (e.g., Bluetooth) can be established. For instance, in an exemplary embodiment, a charger and an implantable battery and/or communication module can each include near field communication components for establishing a secure, near field communication and subsequently pairing to each other for additional wireless communication.

In embodiments wherein the external device includes, or is in communication with, a microphone, the external device can be configured to reprogram the signal processor based on information collected from the microphone representative of the acoustic environment. For example, the external device can be configured to identify background noise (e.g. low-end noise) and update the signal processor transfer function accordingly. In some such examples, the external device can be configured to reduce gain for low-end signals and/or emphasize other sounds or frequency ranges, such as speech or other sounds having a higher frequency. In some embodiments, a user can initiate the process of identifying background noise for adjusting the operation of the signal processor via the external device, for example, via a user interface (e.g., a smartphone or tablet touchscreen).

In embodiments in which the external device includes or is in communication with a location sensor and/or a clock, the external device may reprogram the signal processor based on a detected location and/or time. For instance, in an example embodiment, when the external device is located in a place known to be loud (e.g. a mall or sports stadium), the external device can be configured to detect the location and automatically reprogram the signal processor to reduce background noise (e.g., a particular frequency or range of frequencies) and/or reduce the overall gain associated with the transfer function. Similarly, in some examples, when located in a place in which a wearer may wish to particularly recognize speech (e.g., a movie theater) the external device can be configured to reprogram the signal processor to emphasize frequencies associated with speech.

In some examples, the transfer function can be updated to reduce a contribution of identified background noise. In some embodiments, reducing a contribution of identified background noise comprises emphasizing signals having frequency content between approximately 200 Hz and 20 kHz. In some such examples, updating the transfer function to reduce a contribution of the identified background noise comprises emphasizing signals having frequency content between approximately 300 Hz and 8 kHz. Emphasizing signals in such frequency ranges can help emphasize human speech or other similar signals within a noisy environment.

Additionally or alternatively, the external device can be configured to reprogram the signal processor based on a determined time of day. For example, at times when the wearer generally doesn't want to be bothered (e.g. at night), the external device can be configured to lower the volume of all or most sounds. In some examples, the wearer may additionally or alternatively temporarily reprogram the signal processor via the external device to adjust the transfer function of the signal processor (e.g., to reduce volume) for a predetermined amount of time (e.g. 15 minutes, 1 hour, or 1 day).

In some examples, reprogramming the signal processor comprises adjusting the transfer function to effect a relative change (e.g., reduce volume). In some cases, reprogramming the signal processor comprises implementing a predefined transfer function in response to received data, such as location data indicating the wearer is in a particular location. In some such examples, a plurality of pre-programmed transfer functions are stored in a memory and can be implemented based on data acquired via one or more sensors of the external device.

In some embodiments, the external device can be configured to provide an input signal based on audio generated by the external device. For example, the external device can be a smartphone, and can provide an input signal to a wearers implantable battery and/or communication module comprising audio from a phone call, text to speech audio (e.g. reading a text message or an article out loud), and/or media audio (e.g. videos, music, games, etc.). The implantable battery and/or communication module can be configured to relay the input signal to the signal processor for the signal processor to convert into corresponding stimulation signals.

As discussed herein, various devices may be paired to a cochlear implant system. For example, FIG. 9 provides a variety of external devices such as a programmer 900, charger 902, smartphone/tablet 904, Smartwatch/Wearable 906, Fob 908, or the like. Additionally or alternatively, external devices may comprise a remote, a remote microphone, an external device that connects to a TV or other AV components for streaming audio to a cochlear implant, or the like. Several examples of external devices are described herein.

In some embodiments, a user (e.g. a physician, audiologist, or the like) may manually pair various external devices with an implantable cochlear implant system. However when pairing multiple external devices, the process may become burdensome for the user.

Figure 10:
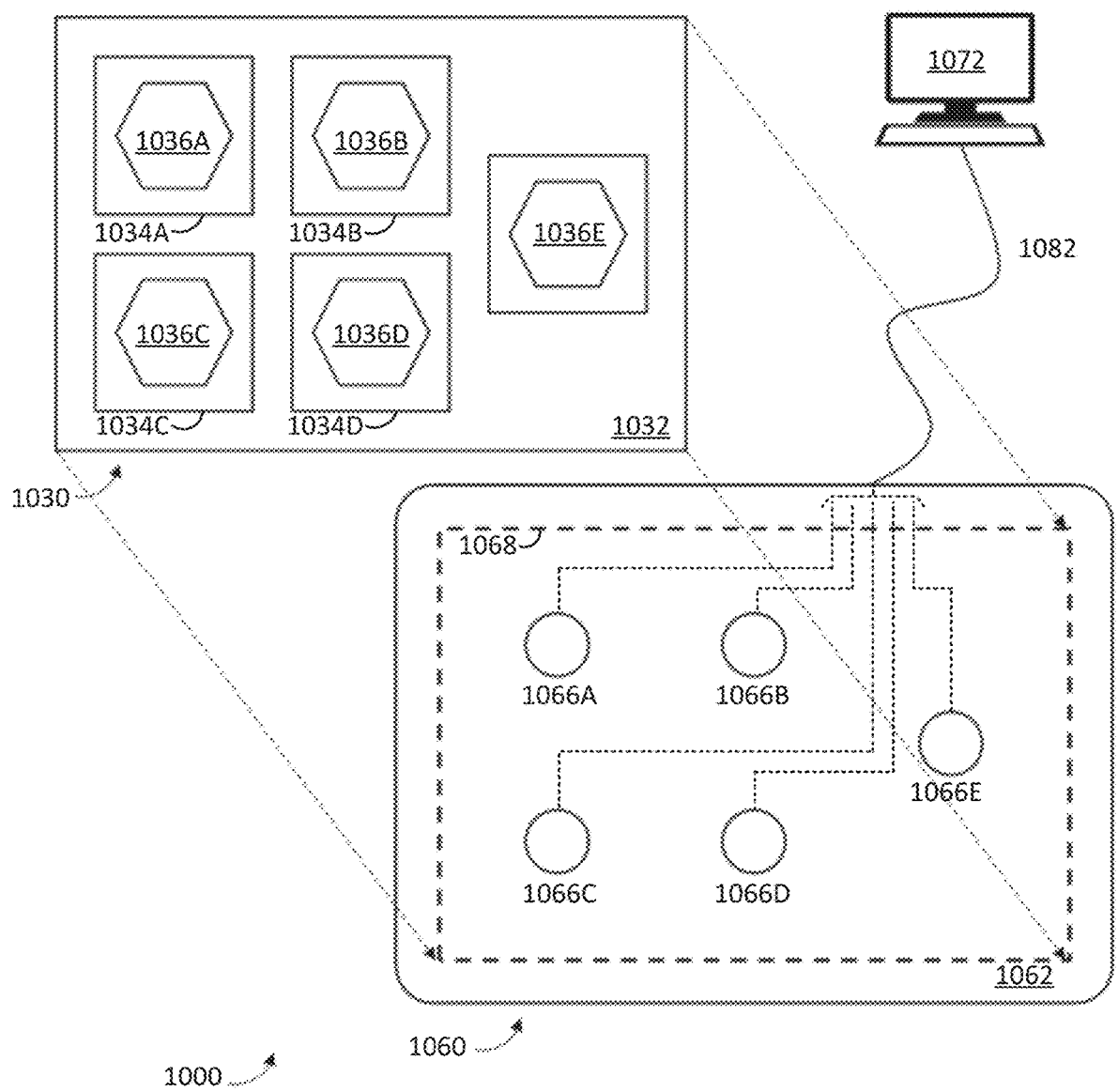
FIG. 10 is an exemplary illustration of an external housing and an external pairing device for pairing one or more external devices with an implantable cochlear implant system.

FIG. 10 shows an illustration of an example pairing system that can be used to facilitate pairing one or more external devices with an implantable cochlear implant system. Such a pairing system can be used to place multiple external devices into communication with a programming device, which can pair each of the external devices with an implantable cochlear implant system.

As shown in the example of FIG. 10, the pairing system 1000 comprises an external pairing device 1060 which can be used to facilitate the pairing of one or more external devices 1036A-E with a cochlear implant system, such as the fully implantable cochlear implant systems shown in FIGS. 1 and 4. The exemplary pairing device may further include a plurality of near field communication devices 1066A-E. Near field communication devices 1066A-E can include, for example, coils that can be configured to communicate and provide electrical power wirelessly.

In some examples, external pairing device 1060 can include a mat, a tabletop, a box, or the like which can provide a relatively flat surface upon which the one or more external devices 1036A-E can be placed, such as the top or side surface of the external pairing device. In some embodiments, each of the near field communication devices 1066A-E may be located beneath such a surface such that one or more external devices positioned on the surface may be positioned proximate a near field communication device and communicate therewith.

Near field communication devices 1066A-E can be configured to provide communication between a programming device 1072 and the one or more external devices 1036A-E. Programming device 1072 can be configured to communicate with the one or more external devices 1036A-E, for example, to enable communication between such external device(s) and an implanted cochlear implant system as described elsewhere herein. In some embodiments, programming device 1072 can include a computer, tablet, smartphone, or other device. In the illustrated example, external pairing device 1060 is in communication with programming device 1072 via a wired connection 1082. As shown, in the example of FIG. 10, each near field communication device 1066A-E has a lead extending from the device to wired connection 1082. In some examples, the wired connection 1082 from the external pairing device is configured to provide parallel communication between each of the near field communication devices and the programming device 1072. For example, in some embodiments, a programming device can be in communication with each of a plurality of external devices (e.g., 1036A-E) simultaneously. In other examples, external pairing device 1060 includes an electronics module configured to multiplex communications between each of the near field communication devices 1066A-E and the programming device 1072. In some such embodiments the programming device 1072 can communicate with each of the near field communication devices 1066A-E individually and can communicate with a plurality of near field communication devices sequentially. Additionally or alternatively, in some examples, external pairing device 1060 can be configured to communicate wirelessly with programming device 1072, such as via a Bluetooth or other wireless communication.

In some embodiments, communication between the programming device 1072 and the one or more external devices 1036A-E is established when the one or more external devices 1036A-E are located adjacent to a corresponding near field communication device 1066A-E.

In some embodiments, an external housing 1030 may be used to house the one or more external devices 1036A-E and assist in placing the one or more external devices 1036A-E adjacent to the one or more corresponding near field communication devices 1066A-E. In some embodiments, the external housing 1030 may comprise any object which can house one or more external devices 1036A-E, such as a box, a briefcase, various containers, or the like.

In some embodiments, the external housing 1030 may comprise one or more compartments 1034A-E. As illustrated in FIG. 10, each of the one or more compartments 1034A-E may comprise a similar geometrical shape. Alternatively, the one or more compartments may comprise a variety of geometrical shapes. In some embodiments, one or more of the one or more compartments 1034A-E may be shaped to receive a unique corresponding external device. In such embodiments, the compartments may comprise indicia, such as labels, notifying a user which unique external device should be placed in said compartment.

In some embodiments, the external housing 1030 may comprise at least one relatively flat surface proximate the one or more compartments 1034A-E that can be placed adjacent to a similarly flat surface of the external pairing device 1060. For instance, in some examples, the external housing 1030 includes a first surface 1032 configured to engage a second surface 1062 included on the external pairing device 1060.

As shown in FIG. 10, the compartments 1034A-E may be arranged in a pattern to facilitate alignment of one or more external devices (e.g. external devices 1036A-E) with a corresponding one or more near field communication devices (e.g. near field communication devices 1066A-E of the external pairing device 1060). Such alignment can result in each of the one or more external devices 1036A-E being positioned near enough to a corresponding one of the near field communication devices 1066A-E to establish communication with the corresponding near field communication device. Established communication between an external device (e.g., 1036A) and a corresponding near field communication device (e.g., 1066A) can result in established communication between the external device (e.g., 1036A) and the programming device 1072 via the near field communication device (e.g., 1066A).

In some embodiments, each of the one or more compartments 1034A-E may be arranged in a first configuration such that each of the one or more compartments 1034A-E has a unique position within the external housing relative to the first surface 1032. In some examples, each of the one or more near field communication devices 1066A-E is arranged in a corresponding configuration relative to the second surface 1062 of the external pairing device 1060. The corresponding configuration can be such that each of the one or more near field communication devices 1066A-E of the external pairing device 1060 can be simultaneously aligned with a corresponding compartment 1034A-E of the external housing 1030. Similarly, each of one or more external devices 1036A-E within a corresponding compartment 1034A-E can simultaneously align with a corresponding one of the one or more near field communication devices 1066A-E.

Additionally or alternatively, in some embodiments, indicia or other markings may be used to assist in providing a correct alignment between the one or more compartments 1034A-E and corresponding near field communication devices 1066A-E. For example, indicia 1068 can be present on the second surface 1062 of the external pairing device 1060 to represent a location and an orientation for positioning the external housing 1030 for correct alignment. Other markings may include indicia on the external housing 1030, bumps or indentations to provide information on a location and orientation for positioning the external housing 1030, or the like.

In addition to facilitate pairing, the external pairing device 1060 may also be configured to electronically charge one or more external devices 1036A-E. For example, the external pairing device 1060 can provide electrical power to one or more external devices 1036A-E via corresponding near field communication devices 1066A-E when an external device 1036A-E is aligned with a corresponding near field communication device 1066A-E. As described elsewhere herein, a near field communication device (e.g., 1066A) can comprise a coil configured to facilitate communication with and charging of a corresponding external device (e.g., 1036A). In various embodiments, electrical power can be provided via the programming device (e.g., via USB connection) and/or an external power source, such as from a wall receptacle, USB port, or the like. In some examples, each near field communication device can include a corresponding drive circuit configured to provide an AC signal to the near field communication device even if receiving power from a DC power source.

In some examples, every near field communication device is able to provide electrical power to charge a corresponding external device simultaneously regardless of which or how many external devices are in communication with the programming device 1072. Some such examples include a connection to a separate power source, such as a wall outlet. In other examples, only those devices in communication with the programming device 1072 receive electrical power, for example, from the programming device 1072 itself While generally described herein with respect to cochlear implant systems (e.g., fully implantable cochlear implant systems), it will be appreciated that configurations such as those shown in FIG. 10 can be used in a variety of applications. In general, an external pairing device including a plurality of near field communication devices can be used to charge and/or communicate with a plurality of devices within an external housing arranged in a configuration corresponding to the configuration of the plurality of near field communication devices. Such systems can be used, for example, to pair each of the plurality of devices to a wireless device. This can be useful when the wireless device does not have an interface via which a user can initiate pairing with the wireless device itself and/or when a plurality of devices are to be paired with the wireless device. Such systems can be implemented, for example, in a medical device context, such as when one or more external devices are to be paired (e.g., placed into wireless communication) with an implanted medical device.

Figure 11:
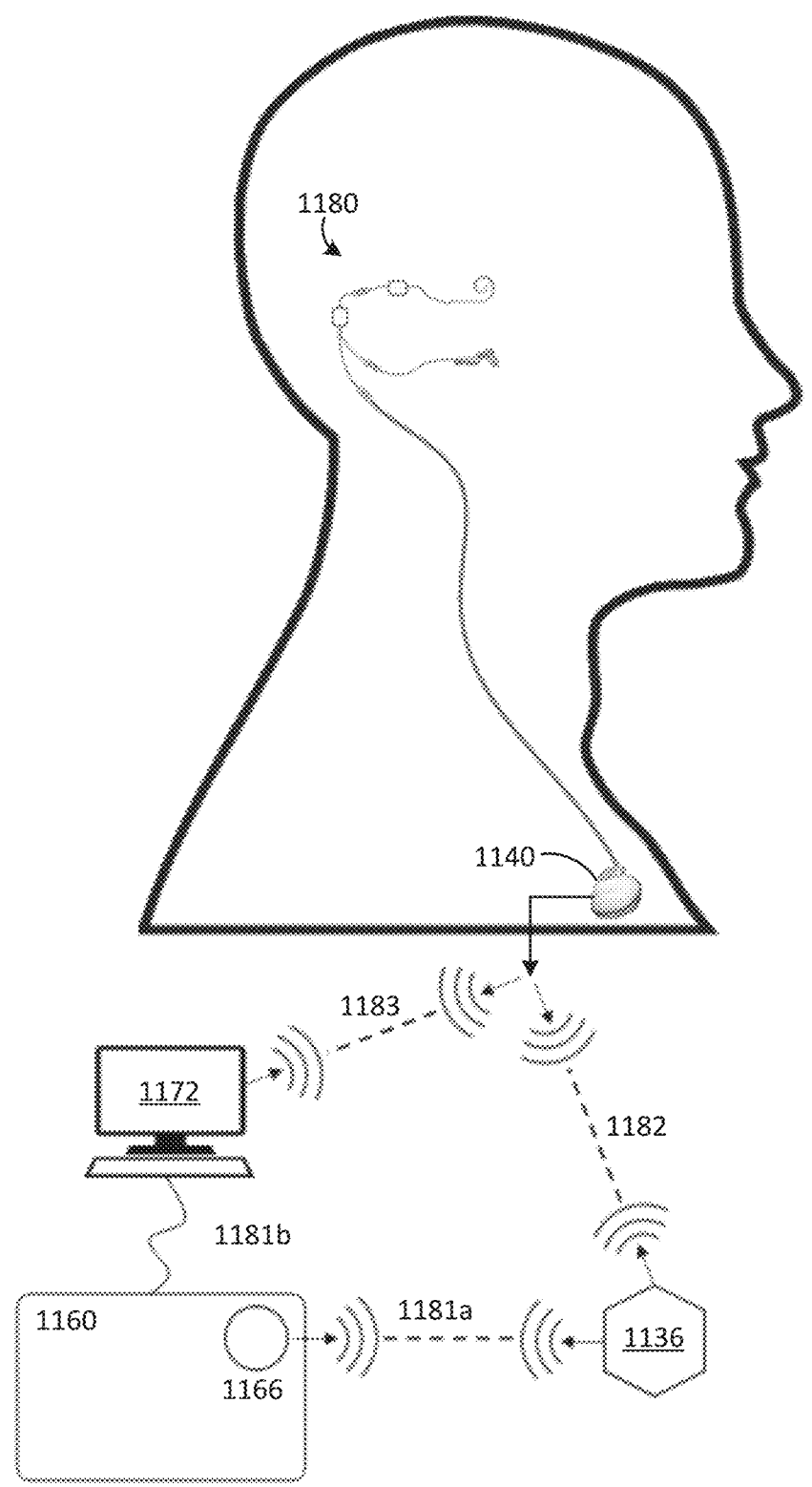
FIG. 11 is an exemplary illustration of an external device establishing a connection with an implantable cochlear implant system and a programming device.

FIG. 11 shows an example illustration of how a programming device and external pairing device can be used to establish a connection between an external device and an implanted cochlear implant system. For simplicity, FIG. 11 illustrates a single external device 1136, however, in various embodiments, a plurality of external devices and corresponding near field communication devices can be used, for example, as described with respect to FIG. 10 and elsewhere herein. As shown in FIG. 11, external device 1136 may establish communication with a near field communication device 1166 of an external pairing device 1160 via a first wireless communication link 1181a, for example, as discussed with respect to FIG. 10 and elsewhere herein. In some embodiments, near field communication device 1166 can include a coil configured to communicate wirelessly with a corresponding coil in the external device 1136.

In some embodiments, the near field communication device 1166 can be connected to a programming device (e.g. programming device 1172), shown in FIG. 11 via communication link 1181b. While shown as being a wired connection in FIG. 11, in various embodiments, communication link 1181b can include a wired or wireless communication link. In some embodiments, the programming device 1172 may be in communication with the external device 1136 through external pairing device 1160 and near field communication device 1166 (e.g., via communication link 1181b and wireless communication link 1181a).

Additionally or alternatively, in some embodiments, the programming device 1172 may communicate directly with external device 1136, such as via a wireless communication link. In such embodiments, external pairing device 1160 may help facilitate initiating the communication between external device 1136 and programming device 1172. For example, in some embodiments, near field communication between external device 1136 and programming device 1172 (via the external pairing device 1160 and wireless communication link 1181a) can be used to enable additional wireless communication (e.g., Bluetooth communication) between the programming device 1172 and the external device 1136, for example, as described in U.S. patent application Ser. No. 16/797,396, filed Feb. 21, 2020, which is assigned to the assignee of the instant application and is incorporated by reference.

In some embodiments, once communication is established between the programming device 1172 and the external device 1136 (e.g. via near field communication device 1166 of external pairing device 1160), the programming device 1172 may be configured to enable communication between the external device 1136 and an implanted cochlear implant system 1180 such as those systems described herein (e.g., a fully implantable cochlear implant system such as shown in FIGS. 1 and 4).

Enabling communication between the external device 1136 and the implanted cochlear implant system 1180 may comprise providing information to the external device 1136 to allow communication between the external device 1136 and the implanted cochlear implant system 1180 to be established, such as via communication link 1182. In some embodiments, the programming device 1172 can be configured to communicate information to the external device 1136 to facilitate wireless communication (e.g., Bluetooth communication) between the external device 1136 and one or more components of the implanted cochlear implant system 1180 (e.g., an implantable battery and/or communication module 1140).

As shown in FIG. 11, the implanted cochlear implant system 1180 comprises an implantable battery and/or communication module 1140 configured to communicate with external sources (e.g. external device 1136, programming device 1172, or the like). In some embodiments, the implantable battery and/or communication module 1140 may be configured to send and/or receive wireless communication signals, such as via communication links 1182 and/or 1183. In various examples, wireless communication links 1182 and 1183 may comprise a wireless connection such as a Bluetooth connection, a Wi-Fi connection, or the like. Accordingly, in some such examples, information provided to the external device 1136 to enable communication between the external device 1136 and the implanted cochlear implant system 1180 can be information enabling Bluetooth or other wireless communication between an implantable battery and/or communication module 1140 and the external device 1136.

In some examples, programming device 1172 can communicate a password or other key to the external device 1136 to enable communication with implanted cochlear implant system 1180. Additionally or alternatively, programming device 1172 can communicate identification information to the external device 1136 identifying the implanted cochlear implant system 1180 for which communication is being enabled. Such identification information can include, for example, a media access controller (MAC) address for the implanted cochlear implant system 1180.

Additionally or alternatively, enabling communication between the external device 1136 and the implanted cochlear implant system 1180 may comprise providing information to the implanted cochlear implant system 1180, such as via communication link 1183, to allow communication between the implanted cochlear implant system 1180 and the external device 1136.

In some embodiments, the communicating information from the programming device 1172 to the external device 1136 to enable communication with the implanted cochlear implant system 1180 is performed in response to a user input to the programming device. For instance, in some examples, programming device 1172 includes a user interface via which a user can input information corresponding to the implanted cochlear implant system 1180 for which communication is to be enabled. In some such embodiments, the programming device 1172 includes a database of identifying information by which a user can select the implanted cochlear implant system 1180 for which to enable communication from the database. For example, the programming device 1172 can include fitting software with information associating an implanted cochlear implant system 1180 to its wearer, and a user (e.g., an audiologist) can enable communication with the implanted cochlear implant system 1180 by selecting the wearer's system within such a database.

Additionally or alternatively, in some examples, the programming device 1172 can be configured to receive information from the implanted cochlear implant system 1180 (e.g., via communication link 1183). Such information can be used by the programming device to communicate the necessary information to the external device 1136 to enable communication with the implanted cochlear implant system 1180.

In some embodiments, once information is provided (e.g.-via programming device 1172) to enable communication between the external device 1136 and the implanted cochlear implant system 1180, information enabling communication is saved in a memory (e.g., in the external device 1136 and/or the implanted cochlear implant system 1180). In such examples, subsequent communications between the external device 1136 and the implanted cochlear implant system 1180 can be established without requiring external pairing device 1160 or programming device 1172. Alternatively, subsequent communications between the external device 1136 and the implanted cochlear implant system 1180 may need to be re-enabled by the external pairing device or a similar device.

Figure 12:
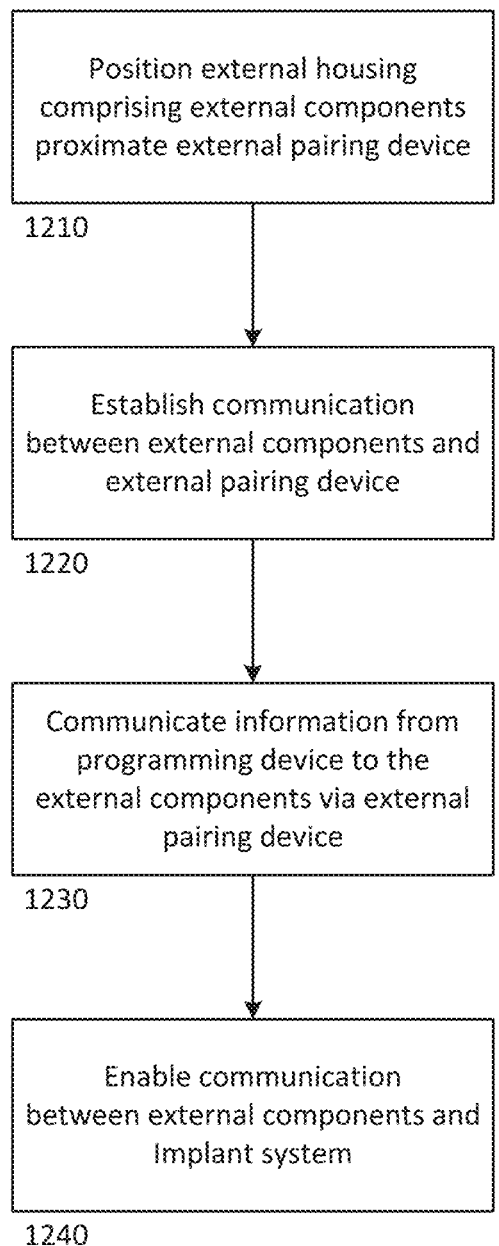
FIG. 12 provides an exemplary method of establishing a connection between an external device and an implantable cochlear implant system.

FIG. 12 illustrates an exemplary method for establishing a connection between an external device and an implantable cochlear implant system as discussed herein. Initially, the one or more external devices (e.g. external devices 1036A-E) may be placed proximate an external pairing device (e.g. external pairing device 1060). In some embodiments, as shown in step 1210, such a step may comprise positioning an external housing (e.g. external housing 1030) comprising the one or more external devices in compartments (e.g. compartments 1034A-E) proximate an external pairing device (e.g. external pairing device 1060). The method further includes establishing communication between the one or more external devices (e.g. external devices 1036A-E) and the external pairing device, such as via the one or more near field communication devices (e.g. near field communication devices 1066A-E) (1220). As discussed herein, establishing communication between external devices and the external pairing device can include aligning each of the one or more external devices with a corresponding near field communication device of the external pairing device.

After communication is established, the method further includes communicating information from a programming device (e.g., 1172) to the external device(s) via the external pairing device (1230). For instance, in some embodiments, information may be communicated to the one or more external devices using a connection between the one or more external devices and the external pairing system, such as via the corresponding near field communication device. Additionally or alternatively, information may be communicated using other means, such as directly from the programming device to the implanted system.

The method shown in FIG. 12 further includes enabling communication between one or more external devices and the implant system (1240). In some embodiments, the information communicated in step 1230 may comprise information to enable communication between the one or more external devices and the implantable cochlear implant system as described elsewhere herein.

As described, in some examples, an external pairing device (e.g., embodied as a mat with one or more coils embedded therein) can provide communication between a programming device and one or more external devices. In some examples, one or more devices paired to an implanted system can be used to subsequently pair additional devices, for example, as described in U.S. patent application Ser. No. 16/797,396, which is incorporated by reference.

Figure 13:
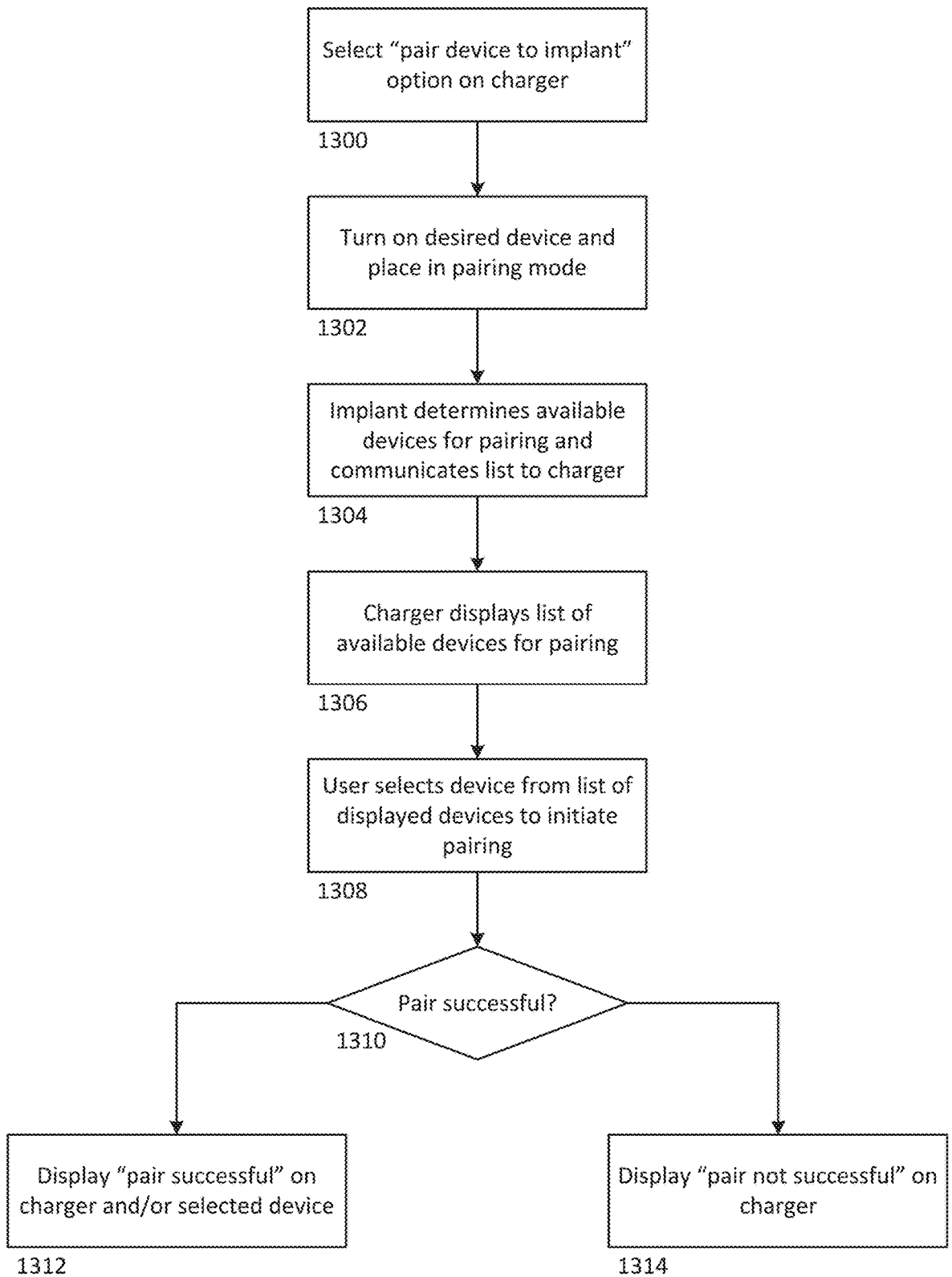
FIG. 13 shows a process flow diagram showing an exemplary method for pairing another device with an implanted system using a paired charger.

FIG. 13 shows a process flow diagram showing an exemplary method for pairing another device with an implanted system using a paired device, in this case, a charger. The method includes selecting an option to pair a device to an implant on the charger (step 1300), turning on the desired device and placing it in a pairing mode (step 1302). The implant determines the devices available for pairing and communicates a list of available devices to the charger (step 1304), which displays the list of available devices to a user (step 1306). The user can select from a list of displayed devices to initiate the pairing (step 1308). The charger and/or selected device can determine if the pairing was successful step (step 1310). If the pairing is successful, a "pair successful" message can be displayed via the charger and/or the newly-paired device (step 1312). If the pair was unsuccessful, a "pair not successful" message can be displayed on the charger (step 1314). For example, in some embodiments, after attempting to initiate pairing between an implant (e.g., via the implantable battery and/or communication module of a system, step 1308), if, after a predetermined amount of time, the charger does not receive an indication confirming pairing from either the implant or the selected device, the charger may determine that the pair was unsuccessful, output the "pair not successful" message (step 1314), and stop attempting to establish the pairing.

In various examples, devices that can be paired to an implant (e.g., for communication with an implantable battery and/or communication module) via the charger such as via the method shown in FIG. 13 can include a remote, a smart device running an application for interfacing with the implant, a fob, an audio streaming device, or other consumer electronics capable of wireless communication (e.g., Bluetooth).

Accordingly, in some examples, an external pairing device and programming device can be used to pair one or more external devices, including a first external device (e.g., a charger), with an implanted system. The first external device can later be used to pair additional external devices to the system such as via the process shown in FIG. 13.

As described, in various embodiments, different external devices can interface with implanted components to adjust operation of the system in various ways. In some embodiments, not all components are capable of performing the same functions as other components. FIG. 14 is a chart showing the various parameters that are adjustable by each of a variety of external devices according to some exemplary systems. In the example of FIG. 14, entries in the chart including an 'X' represent a component configured to perform a corresponding function. Other examples are possible in which different components include different functionality than is represented by the example of FIG. 14, for instance, wherein components other than or in addition to the charger can initiate wireless pairing with the implanted system.

In the illustrated example of FIG. 14, some components can be configured to broadcast an audio stream to the implanted system, such as via a Bluetooth connection. For instance, in some embodiments, an external audio source can broadcast a wireless signal to an implanted system, such as a signal representative of inputs received into the external audio source (e.g., from another media device). Additionally or alternatively, systems can include a remote audio pickup having a microphone or other audio sensing device to receive sounds and to broadcast a wireless signal representative of the received sounds.

In various examples, one or more devices in the chart of FIG. 14 can be prepackaged in an external housing (e.g., housing 1030 of FIG. 10) for delivery to a wearer. As described elsewhere herein, each such device can be located within a corresponding compartment (e.g., 1034A-E) of the external housing. The external housing can be positioned proximate a pairing device and aligned such that each compartment is proximate a corresponding near field communication device. Each external device within a compartment can be placed into communication with a programming device via the corresponding near field communication device. The programming device can be used to pair such external devices with a cochlear implant system, for example, by communicating a MAC address associated with the system to each of the external devices.

In some embodiments, a user may select a prepackaged set of external devices, for example, from a list of available packages or by creating a custom set of external devices. Such devices can be packaged into an external housing by an audiologist or delivered to an audiologist as a prepacked set of external devices. The audiologist can then position the external housing on the external pairing device and use the external pairing device and programming device to pair each external device in the external housing to a wearer's implanted cochlear implant system without having to remove any device from its packaging. Moreover, as described herein, the near field communication devices of the external pairing device can be used to provide electrical power to and charge the external devices. Accordingly, and audiologist can at least partially charge a plurality of external devices and pair such devices to a wearer's implanted cochlear implant system without removing any such devices from the packaging. The audiologist can show the wearer how the external devices work using in-office models while the wearer's external devices remain in their packaging.

As described herein, in some embodiments, a first surface (e.g., 1032) of an external housing (e.g., 1030) and a corresponding second surface (e.g., 1062) of an external pairing device (e.g., 1060) can both be flat. In some such examples, the flat first surface of the external housing can be placed on the second flat surface of the external pairing device to enable communication between one or more external devices and a programming device as discussed herein. Similarly, in some examples, the external pairing device can be placed on top of the external housing to similarly establish communication between one or more external devices and a programming device.

In some examples, the first surface and second surface need not be flat. For instance, in some embodiments, at least one of the first surface 1032 and the second surface 1062 can comprise various textures and/or geometrical features, such as angled or curved surfaces. In some such examples, the first and second surface can include complementary shapes such that the compartments arranged in unique positions relative to the first surface are each positioned proximate a corresponding near field communication device in the second surface when the first and second surfaces are aligned.

In various examples, the first and second surface can be generally horizontal surfaces, such as a mat comprising the second surface and one or more coils embedded therein acting as near field communication devices and configured to support a box comprising one or more compartments and the first surface. In other examples, the first and second surface need not be configured horizontally. In an example embodiment, the second surface can be an approximately vertical surface, and the external housing can be placed adjacent the second surface. In some such examples, the external housing can be set down on a surface other than the first surface such that the first surface on the external housing is positioned proximate the second surface. Other configurations are possible and within the scope of this disclosure.

It will be appreciated that, while generally described herein with respect to implantable hearing systems, communication techniques described can be used in a variety of other implantable systems, such as various neuromodulation devices/systems, including, for example, pain management, spinal cord stimulation, brain stimulation (e.g., deep brain stimulation), and the like. Techniques described herein can be used for pairing external devices to a variety of types of systems, such as partially and fully implantable systems.

Various non-limiting embodiments have been described. These and others are within the scope of the following claims.

The invention claimed is:
1. A pairing system comprising:
an external housing having:
a first surface; and
a plurality of compartments arranged in a first configuration such that
each of the plurality of compartments has a unique position within the external housing relative to the first surface; and wherein
each of the plurality of compartments is configured to house an external device capable of wirelessly interfacing with a cochlear implant system;
an external pairing device comprising:
a second surface; and
a plurality of near field communication devices arranged in a configuration corresponding to the first configuration relative to the second surface such that the first surface of the external housing can be aligned with the second surface of the external pairing device in such a way that each of the plurality of near field communication devices aligns with a corresponding one of the plurality of compartments of the external housing; and wherein
the external pairing device is configured to:
provide communication between a programming device and one or more external devices, each contained within a different compartment of the external housing, via one or more corresponding near field communication devices of the external pairing device.

2. The pairing system of claim 1, wherein the external pairing device comprises a mat, and the second surface of the external pairing device corresponds to a top side of the mat.

3. The pairing system of claim 1, wherein the second surface of the external pairing device comprises indicia representing a location and an orientation for positioning the external housing such that each of the plurality of near field communication devices aligns with a corresponding one of the plurality of compartments of the external housing.

4. The pairing system of claim 1, wherein the external housing comprises a box.

5. The pairing system of claim 1, wherein the external pairing device is configured to electrically charge one or more external devices, each contained in a corresponding compartment of the external housing, via a corresponding one or more near field communication device of the external pairing device when the external housing is positioned proximate the external pairing device and each of the plurality of near field communication devices aligns with a corresponding one of the plurality of compartments of the external housing.

6. The pairing system of claim 5, wherein:
each near field communication device comprises a coil configured to facilitate communication with and charging of an external device within a corresponding compartment and having a corresponding coil.

7. The pairing system of claim 1, wherein each of the plurality of compartments is shaped to receive a unique corresponding external device.

8. The pairing system of claim 1, further comprising:
a cochlear implant system;
a programming device in communication with each of the plurality of near field communication devices of the external pairing device; and
one or more external devices configured to interface with one or more components of the cochlear implant system, each of the one or more external devices positioned within a corresponding one of the compartments of the external housing and including a near field communication interface; and wherein
the programming device is configured to:

communicate with each of the one or more external devices via corresponding near field communication devices of the external pairing device; and provide information to each of the one or more external devices to enable communication between each external device and the cochlear implant system.

9. The pairing system of claim 8, wherein
the cochlear implant system comprises:
a stimulator;
a signal processor in communication with the stimulator, the signal processor being programmed with a transfer function and being configured to receive one or more input signals and output a stimulation signal to the stimulator based on the received one or more input signals and the transfer function; and
an implantable battery and/or communication module in communication with the signal processor, the implantable battery and/or communication module; and wherein
the programming device is configured to:
provide information to each of the one or more external devices to enable communication between each external device and the implantable battery and/or communication module of the cochlear implant system.

10. The pairing system of claim 9 wherein providing information to each of the one or more external devices to enable communication between each external device and the implantable battery and/or communication module of the cochlear implant system comprises enabling Bluetooth communication between each external device and the implantable battery and/or communication module of the cochlear implant system.

11. The pairing system of claim 10, wherein for each of the one or more external devices:
once communication between the component and the cochlear implant system is enabled subsequent communication between the external device and the cochlear implant system can be established without enabling communication via the external pairing device.

12. The pairing system of claim 8, wherein the one or more external devices comprises a charger, a remote, a fob, a remote microphone, or a device configurable to stream audio to the cochlear implant system.

13. The pairing system of claim 8, wherein:
the programming device comprises a user interface; and
providing information to each of the one or more external devices to enable communication between each external device and the cochlear implant system comprises receiving an input via the user interface corresponding to the cochlear implant system.

14. The pairing system of claim 1, wherein each of the plurality of near field communication devices of the external pairing device is located beneath the second surface.

15. A method of establishing wireless communication between a plurality of external devices and a cochlear implant system via a first wireless communication protocol, comprising:
positioning an external housing carrying the plurality of external devices in a corresponding plurality of compartments adjacent to an external pairing device such that each of the plurality of external devices is positioned proximate a corresponding near field communication device of the external pairing device, wherein:

the external housing includes a first surface and a plurality of compartments arranged in a first configuration;
each of the plurality of compartments has a unique position within the external housing relative to the first surface; wherein
each of the plurality of external devices is positioned within a corresponding one of the plurality of external devices;
each of the plurality of external devices comprises a near field communication device and a wireless communication device;
the external pairing device comprises a second surface and a plurality of near field communication devices arranged in a configuration corresponding to the first configuration such that the first surface of the external housing can be aligned with the second surface of the external pairing device in such a way that each of the plurality of near field communication devices of the external pairing device aligns with a corresponding one of the plurality of compartments of the external housing; such that
the positioning the external housing adjacent to the external pairing device such that each of the plurality of external devices is positioned proximate a corresponding near field communication device of the external pairing device establishes near field communication between each external device and the external pairing device;
establishing communication between a programming device and each of the plurality of external devices via the external pairing device; and
for each of the plurality of external devices:
communicating information to the external device via its near field communication device and the corresponding near field communication device of the external pairing device; and
enabling communication via the first wireless communication protocol between the wireless communication device of the external device and a cochlear implant system.

16. The method of claim 15, wherein the external pairing device comprises a mat and the external housing comprises a box.

17. The method of claim 15, wherein the second surface of the external pairing device comprises indicia representing a desired location and a desired orientation of the external housing, such that when the second surface of the external pairing device receives the first surface of the external housing at the desired location and in the desired orientation, near field communication is established between each of the plurality of external devices and a corresponding near field communication device of the external pairing device.

18. The method of claim 15, further comprising charging each of the each of the plurality of external devices when the second surface of the external pairing device is placed proximate the first surface of the external housing such that each of the plurality of external devices is positioned proximate a corresponding near field communication device of the external pairing device.

19. The method of claim 15, wherein for each of the plurality of external devices:
once communication between the external device and the cochlear implant system via the first wireless communication protocol is enabled for a first time, subsequent connection between the component and the cochlear implant system can be established without establishing near field communication between the external device and the external pairing device.

20. The method of claim 15, wherein the enabling communication between each of the plurality of external devices and the cochlear implant system via the first wireless communication protocol further comprises receiving, at each external device, information corresponding to the cochlear implant system, the information enabling communication between the external device and the cochlear implant system.

21. The method of claim 20, wherein the received information comprises a media access controller (MAC) address for the cochlear implant system.

22. The method of claim 20, wherein the received information comprises a unique device identifier and one or more encryption keys.

* * * * *